US010058490B2

(12) United States Patent
Casasanta, III et al.

(10) Patent No.: US 10,058,490 B2
(45) Date of Patent: Aug. 28, 2018

(54) ACOUSTICALLY-ACTIVATED COSMETIC HYDROGELS

(71) Applicant: L'Oreal, Paris (FR)

(72) Inventors: Vincenzo Casasanta, III, Woodinville, WA (US); William Brenden Carlson, Seattle, WA (US); Gregory David Phelan, Cortland, NY (US)

(73) Assignee: L'Oreal, Paris (FR)

( * ) Notice: Subject to any disclaimer, the term of this patent is extended or adjusted under 35 U.S.C. 154(b) by 313 days.

(21) Appl. No.: 14/582,816

(22) Filed: Dec. 24, 2014

(65) Prior Publication Data
US 2016/0184193 A1   Jun. 30, 2016

(51) Int. Cl.
| | |
|---|---|
| *A61K 8/02* | (2006.01) |
| *A61K 8/44* | (2006.01) |
| *A61K 8/64* | (2006.01) |
| *A61K 8/73* | (2006.01) |
| *A61Q 19/00* | (2006.01) |
| *A61H 23/00* | (2006.01) |
| *A61K 8/19* | (2006.01) |
| *A61K 8/29* | (2006.01) |
| *A61K 8/60* | (2006.01) |
| *A61N 7/00* | (2006.01) |

(52) U.S. Cl.
CPC ............ *A61K 8/0291* (2013.01); *A61H 23/00* (2013.01); *A61K 8/0241* (2013.01); *A61K 8/19* (2013.01); *A61K 8/29* (2013.01); *A61K 8/44* (2013.01); *A61K 8/60* (2013.01); *A61K 8/64* (2013.01); *A61K 8/731* (2013.01); *A61N 7/00* (2013.01); *A61Q 19/00* (2013.01); *A61Q 19/007* (2013.01); *A61K 2800/42* (2013.01); *A61K 2800/546* (2013.01); *A61K 2800/622* (2013.01); *A61K 2800/654* (2013.01); *A61K 2800/81* (2013.01); *A61K 2800/82* (2013.01)

(58) Field of Classification Search
None
See application file for complete search history.

(56) References Cited

U.S. PATENT DOCUMENTS

| 6,136,864 A | * | 10/2000 | Nichols | A61K 9/2013 |
| | | | | 514/305 |
| 7,670,623 B2 | * | 3/2010 | Kotha | A61K 9/501 |
| | | | | 424/489 |
| 2002/0028954 A1 | | 3/2002 | Khoury et al. | |
| 2004/0241212 A1 | * | 12/2004 | Pendharkar | A61L 15/28 |
| | | | | 424/445 |

FOREIGN PATENT DOCUMENTS

| EP | 2 494 953 A1 | 9/2012 |
| WO | 03/047493 A2 | 6/2003 |
| WO | 03/086215 A1 | 10/2003 |
| WO | 2006/105659 A1 | 10/2006 |
| WO | 2012/057751 A1 | 5/2012 |
| WO | 2013/090357 A1 | 6/2013 |

OTHER PUBLICATIONS

Correa et al. ('A graph-structural method for prediction of polymer properties' Brazilian Journal of Chemical Engineering v21(4) Oct.-Dec. 2004 pp. 621-628).*
Miao X. ('Hydrophobically modified derivatives of polysaccharides' Doctoral Thesis University of Grenoble Oct. 2011 total of 147 pages with pp. i-x and 1-137).*
Shchipunov et al. ('Gelling of otherwise nongelable polysaccharides' Journal of Colloid and Interface Science v287 2005 pp. 373-378).*
Qiu et al. ('Smart materials based on cellulose: a review of the preparations, properties, and applications' Materials v6 2013 pp. 738-781) (Year: 2013).*
International Search Report and Written Opinion dated Feb. 15, 2016, issued in corresponding International Application No. PCT/US2015/062763, filed Nov. 25, 2015, 16 pages.
Rosén, O., et al., "Responsive Polymer Gels Based on Hydrophobically Modified Cellulose Ethers and Their Interactions With Ionic Surfactants," Langmuir 14:(20)5795-5801, Sep. 1998.
Zhang, N., et al., "Polysaccharide-Based Micelles for Drug Delivery," Pharmaceutics 5(2):329-352, May 2013.
International Preliminary Report on Patentability and Written Opinion, dated Jul. 6, 2017, for International Application No. PCT/US2015/062763, filed Nov. 25, 2015, 10 pages.

* cited by examiner

*Primary Examiner* — Karlheinz R. Skowronek
*Assistant Examiner* — Ronald T Niebauer
(74) *Attorney, Agent, or Firm* — Christensen O'Connor Johnson Kindness PLLC

(57) ABSTRACT

A composition that includes an activatable aggregate is described herein. The aggregate has a core and a shell. In some embodiments, when the aggregate is exposed to acoustic energy, the core of the aggregate includes a hydrogel that is capable of absorbing a relatively large amount of water. The core of the aggregate is covalently bound to a shell of linear aliphatic moieties. The aggregate is synthesized to minimize the amount of water in the core, prior to exposure to acoustic energy. Methods of hydrating using the compositions are also provided.

5 Claims, 11 Drawing Sheets

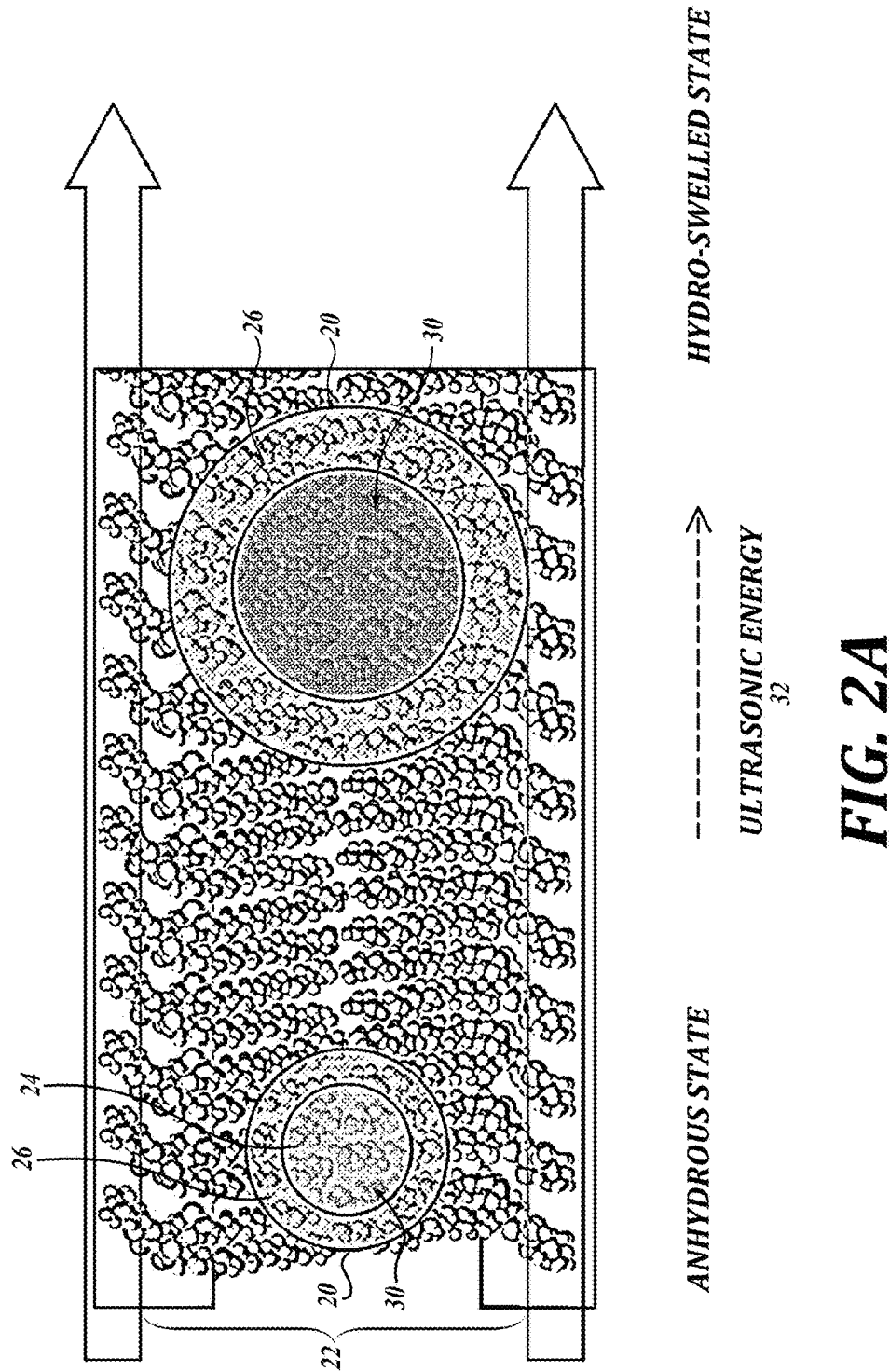

ACOUSTICALLY-ACTIVATED COSMETIC HYDROGELS

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure features a composition, including an aggregate including a core and a shell; the core having a polysaccharide, a crosslinked saccharide, a crosslinked amino acid, or a crosslinked peptide; and the shell having an aliphatic moiety covalently bonded to the core.

In another aspect, the present disclosure features an aggregate including a polymer of Formula (I)

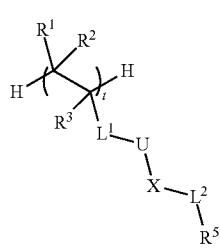

(I)

wherein:

$R^1$, $R^2$, and $R^3$ are each independently selected from H and $C_{1-6}$ alkyl;

$L^1$ is selected from —C(O)O—, —O—, —C(O)NH—, —C(O)NC$_{1-3}$ alkyl-, —OC(O)NH—, —OC(O)NC$_{1-3}$alkyl-, and —OCH$_2$O—;

U is independently selected from a saccharide and a disaccharide, each substituted with 1, 2, 3, 4, 5, or 6 $R^4$ selected from OH, $C_{1-4}$ alkyl-OH, and $C_{1-3}$ alkoxy;

$R^5$ is $C_{4-24}$ alkyl;

X is $C_{1-4}$ alkylene optionally substituted by 1, 2, 3, or 4 OH;

$L^2$ is selected from —O—, —C(O)O—, —C(O)NH—, —C(O)NC$_{1-3}$ alkyl-, —OP(O)(OH)O—, and —S—; and t is an integer of from 2 to 50.

In another aspect, the present disclosure features an aggregate including a polymer of Formula (II)

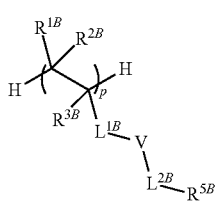

(II)

wherein:

$R^{1B}$, $R^{2B}$, and $R^{3B}$ are each independently selected from H and $C_{1-6}$ alkyl;

$L^{1B}$ is —C(O)NH— or —C(O)NC$_{1-4}$ alkyl-;

V is independently selected from an amino acid residue and a peptide residue including between 2 and 50 amino acid residues;

$L^{2B}$ is —C(O)O—;

$R^{5B}$ is $C_{4-24}$ alkyl; and p is an integer of from 2 to 50.

In another aspect, the present disclosure features a composition, including an aggregate including a core including a crosslinkable saccharide, a crosslinkable polysaccharide, a crosslinkable amino acid, or a crosslinkable peptide; and a shell including an aliphatic moiety, wherein the aliphatic moiety is covalently bonded to the core.

In yet another aspect, the present disclosure features an aggregate including a compound of Formula (I-1)

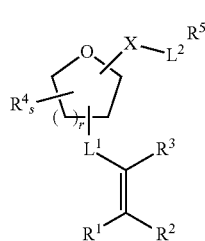

(I-2)

wherein:

$R^1$, $R^2$, and $R^3$ are each independently selected from H and $C_{1-6}$ alkyl;

$R^4$ is selected from OH, $C_{1-4}$ alkyl-OH, and $C_{1-3}$ alkoxy;

$R^5$ is $C_{4-24}$ alkyl;

X is $C_{1-4}$ alkylene optionally substituted by 1, 2, 3, or 4 OH;

$L^1$ is selected from —C(O)O—, —O—, —C(O)NH—, —C(O)NC$_{1-3}$ alkyl-, —OC(O)NH—, —OC(O)NC$_{1-3}$alkyl-, and —OCH$_2$O—

$L^2$ is selected from —O—, —C(O)O—, —C(O)NH—, —C(O)NC$_{1-3}$ alkyl-, —OP(O)(OH)O—, and —S—;

r is 1 or 2; and s is 1, 2, 3, 4, 5, or 6.

In yet another aspect, the present disclosure features an aggregate including a compound of Formula (II-1)

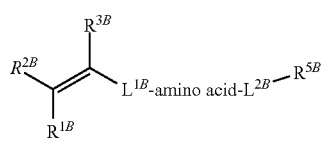

(II-1)

wherein:

$R^{1B}$, $R^{2B}$, and $R^{3B}$ are each independently selected from H and $C_{1-6}$ alkyl;

$L^{1B}$ is —C(O)NH— or —C(O)NC$_{1-4}$ alkyl-;

$L^{2B}$ is —C(O)O—; and $R^{5B}$ is $C_{4-24}$ alkyl.

In yet another aspect, the present disclosure features an aggregate including a compound of Formula (II-2)

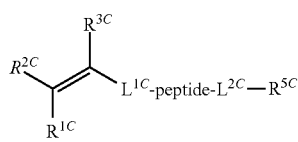

(II-2)

wherein:

$R^{1C}$, $R^{2C}$, and $R^{3C}$ are each independently selected from H and $C_{1-6}$ alkyl;

$L^{1C}$ is —C(O)NH— or —C(O)N$C_{1-4}$ alkyl-;

$L^{2C}$ is —C(O)O—;

$R^{5C}$ is $C_{4-24}$ alkyl; and the peptides includes from 2 to 50 amino acids.

In yet another aspect, the present disclosure features a method of hydrating skin, including applying any one of the compositions above to a skin portion in an amount and for a duration sufficient for an aggregate to absorb into an epidermal layer of a skin portion; and swelling the core of the absorbed aggregate in the epidermal layer by applying an acoustic stimulus of a character and for a duration sufficient to allow the core to absorb water to provide a swollen absorbed aggregate.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein:

FIG. 2A is a schematic representation of an embodiment of aggregates of the present disclosure;

DETAILED DESCRIPTION

The epidermis is the outer layer of the skin and the outermost portion of the epidermis is known as the stratum corneum. As the stratum corneum forms the outermost skin layer, cosmetic agents are often applied to the stratum corneum to provide beneficial cosmetic effects such as increased moisture retention and decreased appearance of wrinkles and fine lines.

Figure 1:
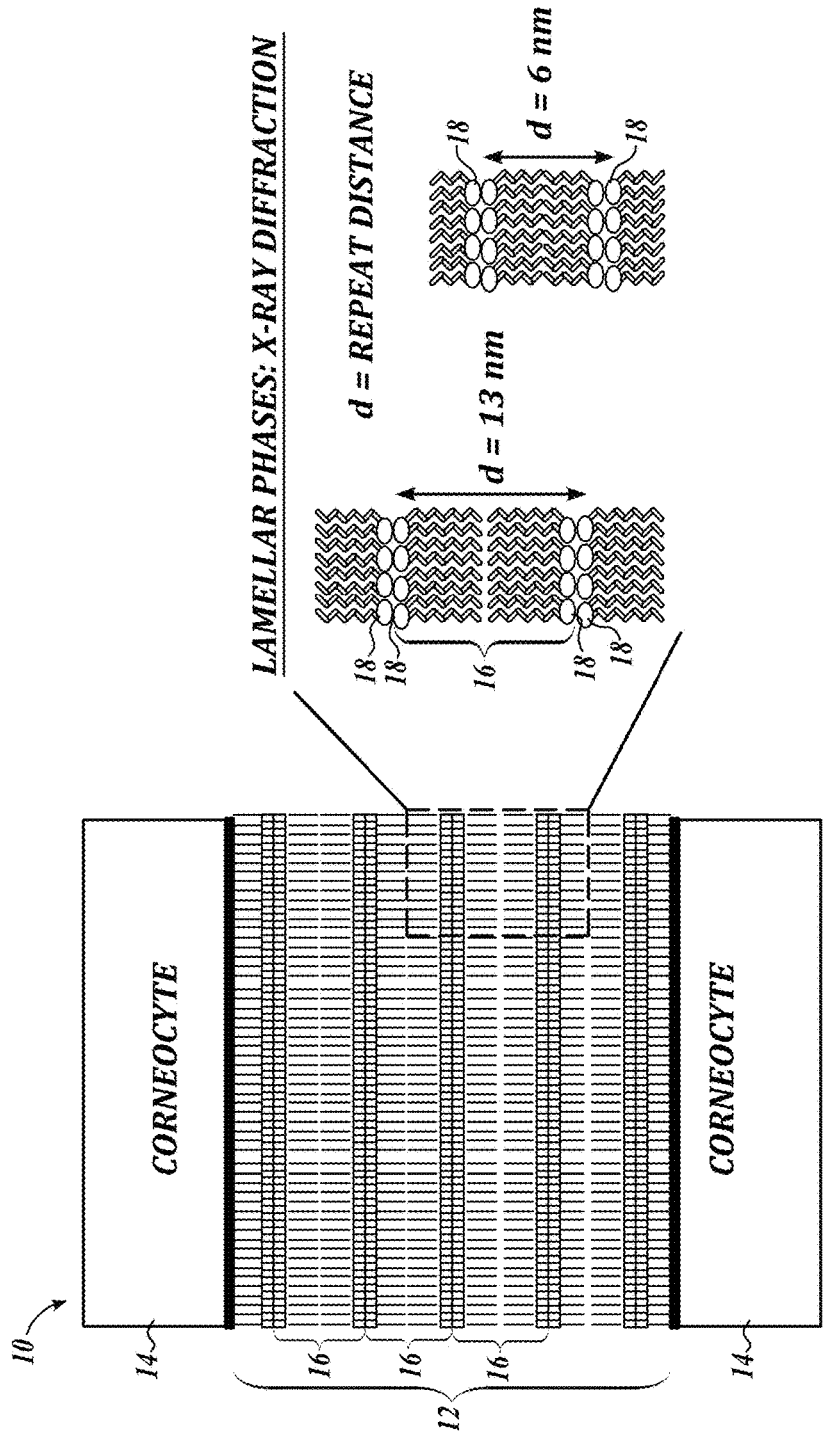
FIG. 1 is a schematic representation of lipid bilayers forming intercellular boundaries between corneocytes of the stratum corneum (i.e., outermost part of the epidermis)

Referring to FIG. 1, the intercellular regions 12 between the corneocytes 14 of the stratum corneum 10 of skin consist of several lipid bilayers 16. These lipid layers 16 contain ceramides, fatty acids, and cholesterols. X-ray diffraction measurements have shown that layers 16 have thickness in the ranges of 6-13 nm. The hydrophilic head-groups 18 of bilayers 16 form an aqueous phase that has been shown to actively transport water throughout the intercellular boundaries of stratum corneum 10.

Disclosed herein are stimuli-responsive compositions that include polymers that can be activated to absorb water using a particular type of stimulus. Also disclosed herein are methods of using the compositions. Such stimuli-responsive compositions are advantageous because their properties are controlled by the presence or absence of the stimulus. For example, some compositions undergo a structural or compositional change when exposed to a stimulus that initiates or promotes a chemical reaction. In exemplary applications of the disclosed embodiments, a composition that is coupled with skin care device that provides an acoustic stimulus is particularly advantageous, as the composition utilizes the mechanical energies from the skin care device (e.g., in the form of acoustic vibrations) to provide beneficial cosmetic effects to a skin area to which the composition has been applied.

In some embodiments, a composition that includes an aggregate that is activatable using acoustic energy. Non-limiting examples of aggregates include covalently bonded assemblies of molecules (e.g., polymers), non-covalently bonded (e.g., ionically bonded, hydrogen bonded) assemblies of molecules (e.g., polymers), complexes, macromolecules, and the like. In an embodiment, the aggregate includes a shell and a core. In an embodiment, the aggregate includes a shell covalently bonded to a core.

In some embodiments, a composition that includes an aggregate including a shell and a core is infused into the stratum corneum or upper layers of the epidermis. Once integrated into any one of the cellular or intercellular structures, the activatable aggregate is excited by acoustic energy (e.g., sonic energy, ultrasonic energy, and the like). Upon excitation, a structural change occurs in the aggregate such that the aggregate absorbs water (i.e., the aggregate is activated to absorb water).

Figure 2B:
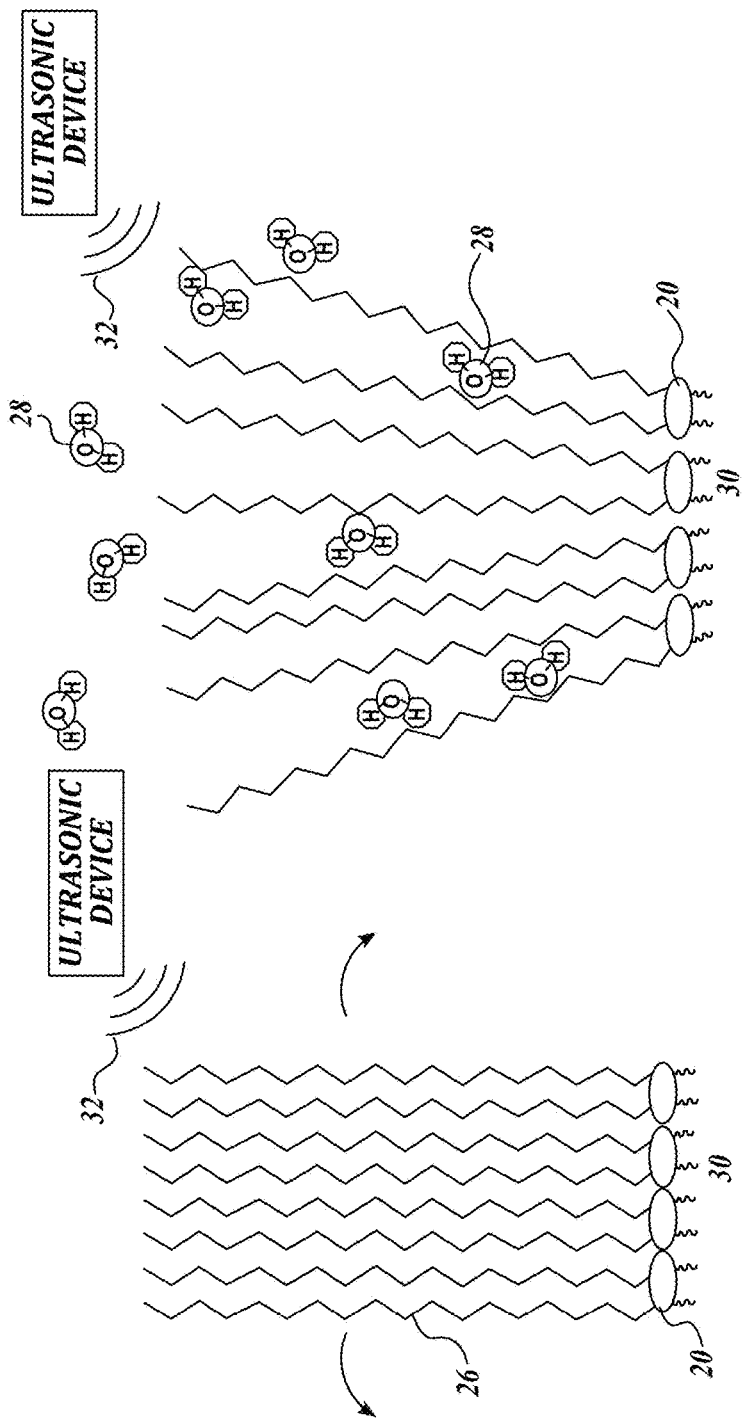
FIG. 2B is a schematic representation of acoustic disruption of lipid organization on an embodiment of aggregates of the present disclosure.

The activatable aggregate can lodge in the lipid bilayers boundaries of the corneocytes. For example, referring to FIG. 2A, an aggregate 20 has a size scale corresponding to or smaller than the lipid bilayers 22 of the intercellular boundaries of the stratum corneum, such that an anhydrous aggregate 20 becomes lodged in the lipid phase of the bilayers. In some embodiments, the infusion of the aggregates into the bilayer lipid phase is facilitated by percutaneous absorption enhancers such as oleic acid. Aggregate 20 has a crosslinked core 30 and a covalently-bound shell 26. Once situated in the lipid phase of the intercellular bilayers 22 of the stratum corneum, the aggregate is in an initial state 24 where its outer ordered aliphatic layer 26 is miscible with the lipid phase. Referring to FIG. 2B, upon ultrasonic excitation 32, the packing order of the aliphatic shell 26 of aggregate 20 is disrupted such that water 28 from the aqueous phase in the intercellular bilayer 22 diffuses into the interior core 30 of aggregate 20. Referring back to FIG. 2A, the interior core 30 is a crosslinked hydrogel capable of absorbing and swelling with water 28 and thus increasing in volume until, for example, saturation. When a sufficient amount of aggregates is located in the intercellular space of the corneocytes, a reduction of fine lines and wrinkles is observed in the skin area containing the aggregates.

Definitions

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl. It is also intended that a linking group definition encompasses both forward and reverse directions. For example, when a variable for a linking group is —C(O)NH— (an amide), it is intended that the amide encompasses both —C(O)NH— and —NHC(O)—. As another example, when a linking group is —C(O)O— (an ester), it is intended that the ester encompasses both —C(O)O— and —OC(O)—.

It is further appreciated that certain features of the disclosure, which are, for clarity, described in the context of separate embodiments, can also be provided in combination in a single embodiment.

Conversely, various features of the disclosure which are, for brevity, described in the context of a single embodiment, can also be provided separately or in any suitable subcombination.

As used herein, the expression "between XX and YY" refers to a range of from XX to YY that includes the endpoints XX and YY.

As used herein, "polymer" refers to a chemical compound that is the result of polymerization of two or more repeating constitutional units (e.g., five or more repeating constitutional units, 10 or more repeating constitutional units). As used herein, polymer includes oligomers, which include from two to about 10 constitutional units.

As used herein, the term "copolymer" refers to a polymer that is the result of polymerization of two or more different monomers. In some embodiments, the number and the nature of each constitutional unit are separately controlled in a copolymer. In some embodiments, the constitutional units are disposed in a purely random, an alternating random, a regular alternating, a regular block, or a random block configuration unless expressly stated to be otherwise. A purely random configuration can, for example, be: x-x-y-z-x-y-z-y-z-z-z . . . or y-z-x-y-z-y-z-x-x . . . . An alternating random configuration can be: x-y-x-z-y-x-y-z-y-x-z . . . , and a regular alternating configuration can be: x-y-z-x-y-z-x-y-z . . . . A regular block configuration has the following general configuration: . . . x-x-x-y-y-y-z-z-z-x-x-x . . . , while a random block configuration has the general configuration: . . . x-x-x-z-z-x-x-y-y-y-z-z-z-x-x-z-z-z- . . . .

As used herein, the term "substituted" or "substitution" is meant to refer to the replacing of a hydrogen atom with a substituent other than H. For example, an "N-substituted piperidin-4-yl" refers to replacement of the H atom from the NH of the piperidinyl with a non-hydrogen substituent such as, for example, alkyl.

As used herein, "aliphatic," "aliphatic group," or "aliphatic moiety" refers to a hydrocarbon moiety that is straight-chain (i.e., unbranched), branched, or cyclic (including fused, bridging, and spiro-fused polycyclic) and that is completely saturated or that contains one or more units of unsaturation, but which is not aromatic. Unless otherwise specified, aliphatic groups contain 1-40 carbon atoms. In certain embodiments, aliphatic groups contain 1-20 carbon atoms. In certain embodiments, aliphatic groups contain 4-24 carbon atoms (e.g., 6-24 carbon atoms, 8-24 carbon atoms, 8-16 carbon atoms, 8-12 carbon atoms, or 12-18 carbon atoms). In certain embodiments, aliphatic groups contain 1-12 carbon atoms. In certain embodiments, aliphatic groups contain 1-8 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

As used herein, "heteroaliphatic" refers to aliphatic groups wherein one or more carbon atoms are independently replaced by one or more atoms selected from the group consisting of oxygen, sulfur, nitrogen, or phosphorus. In certain embodiments, one to six carbon atoms are independently replaced by one or more of oxygen, sulfur, nitrogen, or phosphorus. Heteroaliphatic groups may be substituted or unsubstituted, branched or unbranched, cyclic or acyclic, and/or include saturated, unsaturated or partially unsaturated groups.

As used herein, the term "alkyl" refers to a saturated hydrocarbon group which is straight-chained (e.g., linear) or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. In some embodiments, an alkyl group contains from 1 to about 30, from 1 to about 24, from 2 to about 24, from 1 to about 20, from 2 to about 20, from 1 to about 10, from 1 to about 8, from 1 to about 6, from 1 to about 4, or from 1 to about 3 carbon atoms.

As used herein, the term "alkylene" refers to a linking alkyl group.

As used herein, "alkenyl" refers to an alkyl group having one or more double carbon-carbon bonds. In some embodiments, the alkenyl group is linear or branched. Example alkenyl groups include ethenyl, propenyl, and the like. In some embodiments, an alkenyl group contains from 2 to about 30, from 2 to about 24, from 2 to about 20, from 2 to about 10, from 2 to about 8, from 2 to about 6, or from 2 to about 4 carbon atoms.

As used herein, "alkenylene" refers to a linking alkenyl group.

As used herein, "alkynyl" refers to an alkyl group having one or more triple carbon-carbon bonds. In some embodiments, the alkynyl group is linear or branched. Example alkynyl groups include ethynyl, propynyl, and the like. In some embodiments, an alkynyl group contains from 2 to about 30, from 2 to about 24, from 2 to about 20, from 2 to about 10, from 2 to about 8, from 2 to about 6, or from 2 to about 4 carbon atoms.

As used herein, "alkynylene" refers to a linking alkynyl group.

As used herein, "alkoxy" refers to an —O-alkyl group. Example alkoxy groups include methoxy, ethoxy, propoxy (e.g., n-propoxy and isopropoxy), t-butoxy, and the like.

As used herein, the term "vinyl moiety" refers to the functional group —CH=$CH_2$, which is optionally substituted.

As used herein, the term "aryl" refers to monocyclic or polycyclic (e.g., having 2, 3, or 4 fused rings) aromatic hydrocarbons such as, for example, phenyl, naphthyl, anthracenyl, phenanthrenyl, indanyl, and indenyl. In some embodiments, aryl groups have from 6 to about 20 carbon atoms. In some embodiments, an aryl group is a 5, 6, or 7-membered aromatic ring.

As used herein, the term "halo" or "halogen" includes fluoro, chloro, bromo, and iodo.

As used herein, "crosslink" refers to a bond, atom, or group of atoms that connects two adjacent chains of atoms in a large molecule such as a polymer or protein. In some embodiments, a crosslink connects two adjacent small molecules such as a saccharide, an amino acid, or derivatives thereof. Internal crosslinking between two sites on a single molecule (e.g., a polymer or a protein) is also possible.

As used herein, "hydrogel" refers a substance formed when an organic hydrophilic polymer, (natural or synthetic) that is crosslinked via covalent, ionic, or hydrogen bonds to form a three-dimensional open-lattice network structure that entraps water molecules to form a gel. In some embodiments, hydrogels contains 90% or more water (e.g., 80% or more, 70% or more, 60% or more, or 50% or more) by volume.

As used herein, "molecular weight" of a polymer or a protein refers to a number average molecular weight ($M_n$) that is determined by titration, by vapor phase osmometry, or by gel permeation chromatography.

As used herein, the term "constitutional unit" of a polymer refers an atom or group of atoms in a polymer, including a part of the chain together with its pendant atoms or groups of atoms, if any. In some embodiments, the constitutional unit refers to a repeat unit. In certain embodiments, the constitutional unit refers to an end group on a polymer chain. For example, in some embodiments, the constitutional unit of polyethylene glycol is —$CH_2CH_2O$— corresponding to a repeat unit, or —$CH_2CH_2OH$ corresponding to an end group.

As used herein, the term "repeat unit" corresponds to the smallest constitutional unit, the repetition of which constitutes a regular macromolecule (or oligomer molecule or block).

As used herein, the term "end group" refers to a constitutional unit with only one attachment to a polymer chain, located at the end of a polymer. For example, in some embodiments, the end group is derived from a monomer unit at the end of the polymer, once the monomer unit has been polymerized. As another example, in some embodiments, the end group is a part of a chain transfer agent or initiating agent that was used to synthesize the polymer.

As used herein, the term "terminus" of a polymer refers to a constitutional unit of the polymer that is positioned at the end of a polymer backbone.

As used herein, "amino acid" refers to an organic compound including a primary or secondary amine and a carboxylic acid functional group, with a side chain. Amino acids have a molecular weight of about 500 or less. Non-limiting examples of natural amino acid include histidine, isoleucine, leucine, lysine, methionine, phenylalanine, threonine, tryptophan, valine, alanine, arginine, asparagine, aspartic acid, cysteine, glutamic acid, glutamine, glycine, ornithine, proline, selenocysteine, serine, tyrosine, selenocysteine, pyrrolysine, N-formylmethionine, etc. Non-natural amino acids include, for example, amino acid analogs such as azetidine-2-carboxylic acid, 3,4-dehydroproline, perthiaproline, canavanine, ethionine, norleucine, aminohexanoic acid, homoallylglycine, homopropargylglycine, etc. Non-limiting examples of non-natural amino acids also include sugar amino acids such as N-methyl-glucamine where amino and carboxyl functional groups have been incorporated into a sugar framework (e.g., at the two termini of regular 2,5 or 2,6-anhydro sugar frameworks). In some embodiments, the term "amino acid" also includes "amino acid residues," which are amino acids that are incorporated into a larger molecule, for example, by reaction of the amino or carboxylic acid functional groups with a reactive moiety. When the amino acid is incorporated into a larger molecule, what remains of the amino acid in the larger molecule is generally referred to as an "amino acid residue". For example, the amino acid residue can lack a hydrogen of the amino group, or a hydroxyl moiety of the carboxyl group, or both.

As used herein, "peptide" refers to a chain of amino acid monomers linked by amide bonds. In some embodiments, a peptide includes from 2 amino acid residues to 50 amino acids residues (e.g., from 2 to 20 amino acid residues, from 2 to 10 amino acid residues, or from 5 to 10 amino acid residues).

As used herein, a "saccharide" refers to a carbohydrate of general formula $C_nH_{2n}O_n$, and derivatives of carbohydrates such as sugar alcohols and amino sugars. The saccharide includes acyclic and cyclic forms, which can interconvert through a nucleophilic addition reaction between the carbonyl group and one of the hydroxyls of the same molecule. In some embodiments, the saccharide includes carbohydrates with 3, 4, 5, or 6 carbon atoms. The saccharide residue is a pentose or hexose. Examples of saccharides include glucose, galactose, fructose, ribose, deoxyribose, xylose, sorbitan, sorbitol, mannitol, erythritol, etc.

As used herein, a "disaccharide" refers to a carbohydrate and carbohydrate derivatives formed when two monosaccharides undergo a condensation reaction. Examples of disaccharides include sucrose, lactulose, lactose, maltose, trehalose, cellobiose, kojibiose, nigerose, isomaltose, β,β-trehalose, α,β-trehalose, sophorose, etc.

As used herein, a "polysaccharide" refers to polymeric carbohydrate molecules and polymeric carbohydrate derivatives composed of long chains of monosaccharide units bound together by glycosidic linkages. Examples of polysaccharides include starch, glycogen, cellulose, chitin, and derivatives thereof. As used herein, polysaccharide includes "oligosaccharide," which refers to a saccharide polymer containing 3 to 9 monosaccharides.

As used herein, "activatable" refers to a material that is capable of undergoing a structural or conformational change upon application of a stimulus. The structural or conformational change confers a change in a property, function, or appearance, in the material. For example, in some embodiments, an aggregate has a hydrogel core and an aliphatic shell. When exposed to acoustic energy, the packing order of the aliphatic shell is disrupted, thereby activating and allowing the hydrogel core to absorb water.

As used herein, the term "hydrophilic" refers to a moiety or a molecule that is attracted to and tends to be dissolved by water. The hydrophilic moiety is miscible with an aqueous phase. Hydrophilic molecules are polar and/or ionizable in aqueous conditions. In some embodiments, hydrophilic molecules are ionizable under aqueous conditions and/or contain polar functional groups such as amides, hydroxyl groups, or ethylene glycol residues. Examples of hydrophilic moieties include carboxylic acid groups, amino groups, hydroxyl groups, etc.

As used herein, the term "hydrophobic" refers to a moiety or a molecule that is not attracted to water with significant nonpolar surface area at physiological pH and/or salt conditions. Hydrophobic molecules or moieties tend to be non-polar in aqueous conditions. Examples of hydrophobic moieties include alkyl groups, aryl groups, etc.

As used herein, a "cosmetic composition" refers to a composition suitable for topical application on keratinous tissue.

As used herein, "keratinous tissue" refers to the keratin-containing layers disposed as the outermost protective covering of mammals which include, but are not limited to, skin, hair, nails, and cuticles.

As used herein, "effective amount" refers to an amount sufficient to induce one or more effects to the affected area. Non-limiting examples of effects include a change in skin appearance (e.g., decrease in wrinkles), a change in moisture retention of skin, a change in skin texture, etc.

As used herein, "improve skin condition" or "improving skin condition" includes effecting a visually and/or tactilely perceptible positive change, or benefit, in skin appearance and feel. Benefits that are provided include, but are not limited to, one or more of the following: reducing the appearance of wrinkles, coarse deep lines, fine lines, crevices, bumps, and large pores; thickening of keratinous tissue (e.g., building the epidermis and/or dermis and/or subdermal layers of the skin, and where applicable, the keratinous layers of the nail and hair shaft, to reduce skin, hair, or nail atrophy); increasing the convolution of the dermal-epidermal border (also known as the rete ridges); preventing loss of skin or hair elasticity, for example, due to loss, damage and/or inactivation of functional skin elastin, resulting in such conditions as elastosis, sagging, loss of skin or hair recoil from deformation; reduction in cellulite; change in coloration to the skin, hair, or nails, for example, under-eye circles, blotchiness (e.g., uneven red coloration due to, for example, rosacea), sallowness, etc.

As used herein, the term "signs of skin aging" includes all outward visibly and tactilely perceptible manifestations, as well as any macro- or micro-effects, due to keratinous tissue aging. These signs may result from processes which include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin.

As used herein, "cosmetically acceptable" refers to a composition component that is safe for contact with a human integument.

As used herein, "physiological conditions" refer to a temperature range of about 37 degrees Celsius and a pH of about 7 (e.g., 7.3-7.4).

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Compositions

As discussed above, in some embodiments, a composition includes an activatable aggregate. The aggregate has a core and a shell. In some embodiments, the core of the aggregate includes a hydrogel formed of hydrophilic substances that include carbohydrates, amino acids, or peptides that are capable of absorbing a relatively large amount of water. The core of the aggregate is covalently bound to a shell of linear aliphatic moieties. The aggregate is synthesized to minimize the amount of water in the core, prior to initiation of a stimulus to cause water absorption. In some embodiments, the aggregate is a reverse micelle. In other embodiments, the aggregate has a core that is formed of a polymer that is substantially free (e.g., 90% free by volume, 95% free by volume, or 99% free by volume) of pores having a diameter of about 5 nm or more.

In some embodiments, when the aggregate is exposed to acoustic energy, the crosslinked core is configured to absorb water to cause swelling of the aggregate. For example, the core is configured to swell up to 200% (e.g., up to 175%, up to 150%, up to 125%, or up to 105%) by volume of an initial dry volume when exposed to acoustic energy in the presence of water.

This disclosure provides, inter alia, a composition, including an aggregate including a core that includes a polysaccharide moiety, a crosslinked saccharide moiety (e.g., a monosaccharide moiety, a disaccharide moiety, or an oligosaccharide moiety having 20 or fewer saccharide units), a crosslinked amino acid moiety, or a crosslinked peptide moiety; and a shell surrounding the core of the aggregate that includes an aliphatic moiety. The core is hydrophilic and can absorb large amounts of water while also having stability under physiological conditions. In some embodiments, the core is crosslinked and is a hydrogel. The aliphatic moiety of the shell is covalently bonded to the core (e.g., to the polysaccharide, saccharide, amino acid, or peptide of the core).

Saccharide-Based Aggregates

In some embodiments, the aggregate includes a saccharide-containing polymer of Formula (I)

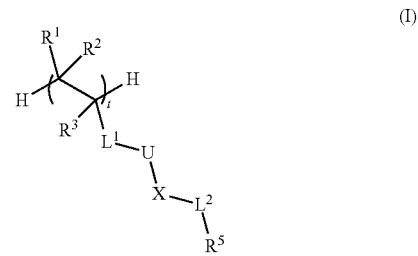

wherein:

$R^1$, $R^2$, and $R^3$ are each independently selected from H and $C_{1-6}$ alkyl;

$L^1$ is selected from —C(O)O—, —O—, —C(O)NH—, —C(O)NC_{1-3} alkyl-, —OC(O)NH—, —OC(O)NC_{1-3}alkyl-, and —OCH$_2$O—;

U is independently selected from a saccharide residue, a disaccharide residue and an oligosaccharide, each substituted with 1, 2, 3, 4, 5, or 6 $R^4$ selected from OH, $C_{1-4}$ alkyl-OH, and $C_{1-3}$ alkoxy;

$R^5$ is $C_{4-24}$ alkyl;

X is $C_{1-4}$ alkylene optionally substituted by 1, 2, 3, or 4 OH;

$L^2$ is selected from —O—, —C(O)O—, —C(O)NH—, —C(O)NC$_{1-3}$ alkyl-, —OP(O)(OH)O—, and —S—; and t is an integer of from 2 to 50.

In some embodiments, $R^1$, $R^2$, and $R^3$ are each H.

In some embodiments, $R^1$, $R^2$, and $R^3$ are each independently selected from H and $C^{1-4}$ alkyl.

In some embodiments, $R^1$, $R^2$, and $R^3$ are each independently selected from H and methyl.

In some embodiments, $R^1$ and $R^2$ are each H and $R^3$ is methyl.

In some embodiments, $L^1$ is selected from —C(O)O—, —O—, —C(O)NH—, —OC(O)NH—, and —OCH$_2$O—.

In some embodiments, $L^1$ is selected from —C(O)O—, —O—, —C(O)NH—, and —OC(O)NH—.

In some embodiments, $L^1$ is selected from —C(O)O—, —O—, and —C(O)NH—.

In some embodiments, $L^1$ is selected from —C(O)O— and —O—.

In some embodiments, $L^1$ is —C(O)O—.

In some embodiments, U is independently selected from a saccharide residue and a disaccharide residue.

In some embodiments, U is an oligosaccharide having 3-10 saccharide constitutional units, such as raffinose or stachyose.

In some embodiments, U is a monosaccharide selected from glucose, galactose, fructose, and sorbitan.

In some embodiments, the disaccharide residue is sucrose, lactulose, lactose, maltose, trehalose, cellobiose, kojibiose, nigerose, isomaltose, β,β-trehalose, α,β-trehalose, or sophorose.

In some embodiments, the disaccharide residue is sucrose, lactose, or maltose.

In some embodiments, $R^4$ is selected from OH and $CH_2OH$.

In some embodiments, X is selected from —$CH_2$— and —$CH_2CH_2$—.

In some embodiments, X is —$CH_2CH_2$—.

In some embodiments, X is —$CH_2$—.

In some embodiments, $L^2$ is selected from —O—, —C(O)O—, and —C(O)NH—.

In some embodiments, $L^2$ is selected from —C(O)O— and —C(O)NH—.

In some embodiments, $L^2$ is —C(O)O—.

In some embodiments, t is an integer of 2 or greater (e.g., 5 or greater, 10 or greater, 20 or greater, 30 or greater, or 40 or greater) and/or 50 or less (e.g., 40 or less, 30 or less, 20 or less, 10 or less, or 5 or less).

In some embodiments, the aggregate includes a polymer of Formula (I-A)

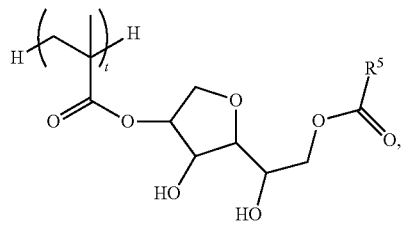

(I-A)

wherein t and $R^5$ are as described above.

In some embodiments, the aggregate includes a polymer of Formula (I-B)

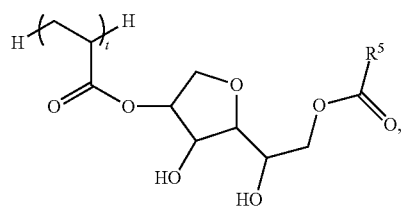

(I-B)

wherein t and $R^5$ are as described above.

In some embodiments, the aggregate includes a polymer of Formula (I-C)

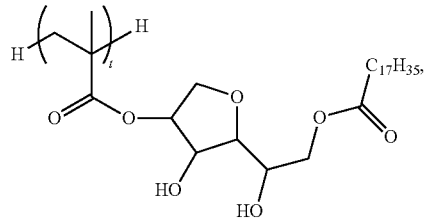

(I-C)

wherein t is as described above.

In some embodiments, the aggregate includes a polymer of Formula (I-D)

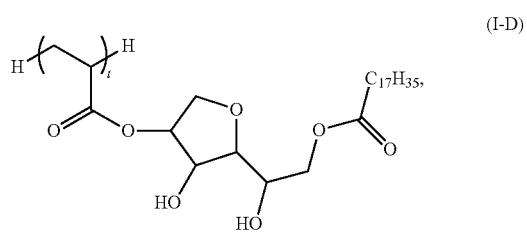

(I-D)

wherein t is as described above.

In some embodiments, the aggregate includes a compound of Formula (I-E)

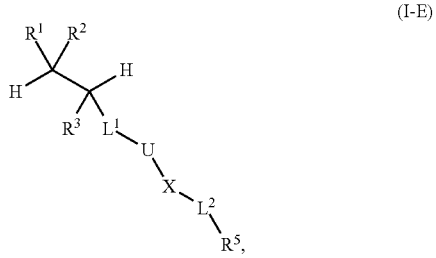

(I-E)

wherein $R^1$, $R^2$, $R^3$, $L^1$, U, X, $L^2$, and $R^5$ are as described above.

In some embodiments, prior to crosslinking to provide an aggregate above that includes a polymer of Formula (I), the aggregate includes a crosslinkable saccharide (e.g., a monosaccharide, a disaccharide) having a covalently bound aliphatic moiety. The crosslinkable saccharide is crosslinked by exposure to a light source and a radical initiator. In some embodiments, the crosslinkable saccharide is functionalized with a crosslinkable moiety (e.g., an optionally substituted vinyl moiety). When crosslinked, an aggregate having a polymer of Formula (I), described above, is provided.

In some embodiments, an aggregate that includes a crosslinkable molecule (e.g., a crosslinkable saccharide) is configured to absorb water. In some embodiments, the aggregate's ability to absorb water and stability are controlled by equilibrium conditions and the concentration of the aggregate.

In some embodiments, prior to crosslinking to provide the aggregate above that includes a polymer of Formula (I), the aggregate includes a crosslinkable compound of Formula (I-1):

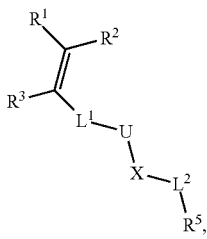

(I-1)

wherein variables $R^1$, $R^2$, $R^3$, $L^1$, U, X, $L^2$, $R^5$ are each as described above.

In some embodiments, prior to crosslinking to provide the aggregate above that includes a polymer of Formula (I), the aggregate includes a crosslinkable compound of Formula (I-2)

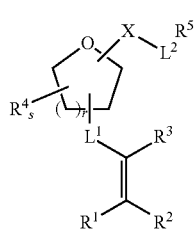

(I-2)

wherein variables $R^1$, $R^2$, $R^3$, $L^1$, U, X, $L^2$, $R^5$ are each as described above.

In some embodiments, the core including a crosslinkable saccharide of Formulae (I-1) or (I-2) is configured to be crosslinked by exposure to ultraviolet light and a radical initiator. In some embodiments, the radical initiator is selected from anthraquinone-2-sulfonic acid sodium salt and 4,4-azobis(4-cyanovaleric acid), which are relatively non-toxic. In some embodiments, the radical initiator is azobisisobutyronitrile. In certain embodiments, the radical initiator is a peroxide.

Example 1, below, describes the synthesis and characterization of aggregates (e.g., permanent reverse micelles) formed of crosslinked saccharides functionalized with an aliphatic moiety.

Polysaccharide-Based Aggregates

In some embodiments, the aggregate includes a core that includes a polysaccharide, such as amylose, amylopectin, glycogen, pectin, hyaluronic acid, methylcellulose, hydroxyethylcellulose (HEC), etc. In some embodiments, the polysaccharide is crosslinked. In other embodiments, the polysaccharide is not crosslinked. In one embodiment, the core includes hydroxyethylcellulose, having the structure shown in Scheme 1.

Scheme 1. Hydroxyethylcellulose structure.

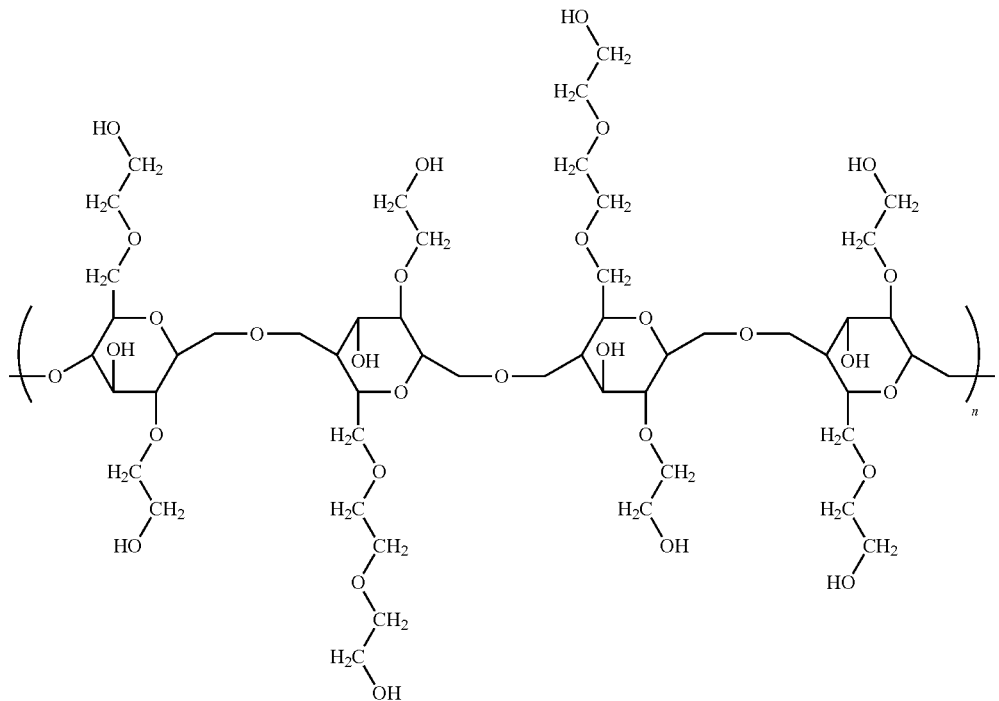

In one embodiment, the polysaccharide (e.g., hydroxyethylcellulose) is functionalized with one or more $C_{4-24}$ alkyl moieties (e.g., one or more $C_{4-12}$ alkyl moieties, one or more $C_4$ alkyl moieties, one or more $C_{10-24}$ alkyl moieties, one or more $C_{12-24}$ alkyl moieties, one or more $C_{16-20}$ alkyl moieties, one or more $C_4$ alkyl moieties, one or more $C_6$ alkyl moieties, one or more $C_8$ alkyl moieties, one or more $C_{10}$ alkyl moieties, one or more $C_{12}$ alkyl moieties, one or more $C_{14}$ alkyl moieties, one or more $C_{16}$ alkyl moieties, one or more $C_{18}$ alkyl moieties, one or more $C_{20}$ alkyl moieties, one or more $C_{22}$ alkyl moieties, or one or more $C_{24}$ alkyl moieties, or any combinations thereof).

In some embodiments, the polysaccharide end groups are each H or OH.

In some embodiments, the $C_{4-24}$ alkyl is covalently bonded to the pendant hydroxyl groups of the polysaccharide (e.g., hydroxyethylcellulose) via a carbamate linkage, an ester linkage, an ether linkage, and/or an amide linkage. Example 3 below and FIG. 9 detail the synthesis of a polysaccharide aggregate that is functionalized an aliphatic shell by reaction of HEC with an alkyl isocyanate.

In some embodiments, a polysaccharide core is first formed, then reacted with a reactive aliphatic molecule to provide an aliphatic shell. In other embodiments, a polysaccharide is first reacted with a reactive aliphatic molecule to provide pendant aliphatic side chains, then an aggregate is formed where the polysaccharide's hydrophilic backbone aggregates in an aggregate core and the aliphatic side chains form a shell around the aggregate core. In some embodiments, a reactive group on the polysaccharide (e.g., a hydroxyl group, an amino group, a carboxylic acid group) reacts spontaneously with a reactive group on an aliphatic molecule (e.g., an acid chloride, a carboxylic acid, an isocyanate group, an amino group, etc.). In some embodiments, the reaction between the polysaccharide and an aliphatic molecule is mediated by a coupling agent (e.g., carbodiimides), and/or is catalyzed (e.g., acid catalyzed, base catalyzed, etc.). In some embodiments, the polysaccharide and/or the aliphatic molecule is activated prior to reaction (e.g., by formation of an N-hydroxysuccinimide ester).

In some embodiments, 3 mole % or more (e.g., 10 mole % or more, 20 mole % or more, 30 mole % or more, or 40 mole % or more) and/or 50 mole % or less (e.g., 40 mole % or less, 30 mole % or less, 20 mole % or less, or 10 mole % or less) of the constitutional units of the polysaccharide is conjugated to a $C_{4-24}$ alkyl. In some embodiments, the molar ratio of the constitutional units of a polysaccharide that is conjugated to a $C_{4-24}$ alkyl to the total constitutional units of the polysaccharide is 1:34 or more (e.g., 1:20 or more, 1:15 or more, 1:10 or more, or 1:5 or more) and/or 1:2 or less (e.g., 1:5 or less, 1:10 or less, 1:15 or less, or 1:20 or less).

In some embodiments, the polysaccharide has a molecular weight of 1,000 or more (e.g., 5,000 or more, 10,000 or more, 50,000 or more, 100,000 or more, 500,000 or more, 1,000,000 or more, or 5,000,000 or more) and/or 10,000,000 or less (e.g., 5,000,000 or less, 1,000,000 or less, 500,000 or less, 100,000 or less, 50,000 or less, or 10,000 or less). For example, the hydroxyethylcellulose has a molecular weight of (e.g., 5,000 or more, 10,000 or more, 50,000 or more, 100,000 or more, 500,000 or more, 1,000,000 or more, or 5,000,000 or more) and/or 10,000,000 or less (e.g., 5,000, 000 or less, 1,000,000 or less, 500,000 or less, 100,000 or less, 50,000 or less, or 10,000 or less).

Amino Acid- or Peptide-Based Aggregates

In some embodiments, the aggregate includes an amino acid- or peptide-containing polymer of Formula (II)

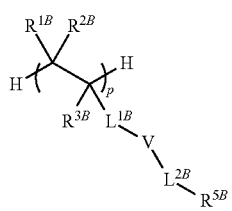

(II)

wherein:

$R^{1B}$, $R^{2B}$, and $R^{3B}$ are each independently selected from H and $C_{1-6}$ alkyl;

$L^{1B}$ is —C(O)NH— or —C(O)N$C_{1-4}$ alkyl-;

V is independently selected from an amino acid residue and a peptide residue including between 2 and 50 amino acid residues;

$L^{2B}$ is —C(O)O—;

$R^{5B}$ is $C_{4-24}$ alkyl; and p is an integer of from 2 to 50.

In some embodiments, $R^{1B}$, $R^{2B}$, and $R^{3B}$ are each H.

In some embodiments, $R^{1B}$, $R^{2B}$, and $R^{3B}$ are each independently selected from H and $C_{1-4}$ alkyl.

In some embodiments, $R^{1B}$, $R^{2B}$, and $R^{3B}$ are each independently selected from H and methyl.

In some embodiments, $R^{1B}$ and $R^{2B}$ are each H and $R^{3B}$ is methyl.

In some embodiments, V is an amino acid residue.

In some embodiments, V is a hydrophilic amino acid residue, such as a sugar amino acid residue, aspartic acid residue, glutamic acid residue, arginine residue, histidine residue, lysine residue, asparagine residue, cysteine residue, glytamine residue, methionine residue, serine residue, and/or threonine residue.

In some embodiments, the amino acid residue is a natural amino acid residue.

In some embodiments, the amino acid residue is a sugar amino acid residue.

In some embodiments, the amino acid residue is a non-natural amino acid residue.

In some embodiments, the amino acid residue is ionized or ionizable at physiological conditions.

In some embodiments, V is a peptide residue including between 2 and 20 amino acid residues (e.g., from 2 to 10 amino acid residues, or from 5 to 10 amino acid residues).

In some embodiments, the peptide residue is hydrophilic.

In some embodiments, the peptide residue is ionized or ionizable at physiological conditions.

In some embodiments, $L^{1B}$ is —C(O)NH—.

In some embodiments, p is an integer of 2 or greater (e.g., 5 or greater, 10 or greater, 20 or greater, 30 or greater, or 40 or greater) and/or 50 or less (e.g., 40 or less, 30 or less, 20 or less, 10 or less, or 5 or less).

In some embodiments, the aggregate includes a compound of Formula (II-A)

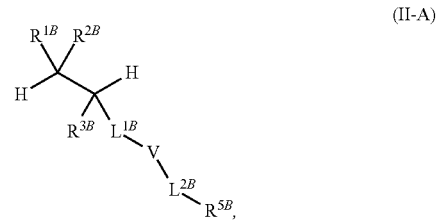

(II-A)

wherein $R^{1B}$, $R^{2B}$, $R^{3B}$, $L^{1B}$, V, $L^{2B}$, and $R^{5B}$ are as described above.

In some embodiments, prior to crosslinking to provide an aggregate above that includes a polymer of Formula (II), the aggregate includes a crosslinkable amino acid or peptide having a covalently bound aliphatic moiety. The crosslinkable amino acid or peptide is crosslinked by exposure to a light source and a radical initiator. In some embodiments, the crosslinkable amino acid or peptide is functionalized with a crosslinkable moiety (e.g., an optionally substituted vinyl moiety). When crosslinked, an aggregate having a polymer of Formula (II), described above, is provided.

In some embodiments, an aggregate that includes a crosslinkable molecule (e.g., a crosslinkable amino acid derivative or a crosslinkable peptide derivative) is configured to absorb water. In some embodiments, the aggregate's ability to absorb water and stability are controlled by equilibrium conditions and the concentration of the aggregate.

In some embodiments, prior to crosslinking to provide the aggregate above that includes a polymer of Formula (II), the aggregate includes a crosslinkable compound of Formula (II-1)

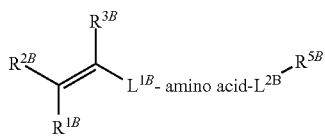

(II-1)

wherein $R^{1B}$, $R^{2B}$, and $R^{3B}$, $L^{1B}$, $L^{2B}$, and $R^{5B}$ are each as described above.

Example 2, below, describes the synthesis and characterization of aggregates (e.g., permanent reverse micelles) formed of crosslinked amino acids functionalized with an aliphatic moiety.

In some embodiments, prior to crosslinking to provide the aggregate above that includes a polymer of Formula (II), the aggregate includes a crosslinkable compound of Formula (II-2)

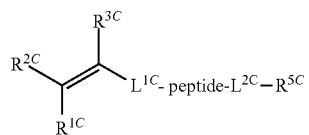

(II-2)

wherein:
$R^{1C}$, $R^{2C}$, and $R^{3C}$ are each independently selected from H and $C_{1-6}$ alkyl;
$L^{1C}$ is —C(O)NH— or —C(O)NC$_{1-4}$ alkyl-;
$L^{2C}$ is —C(O)O—;
$R^{5C}$ is $C_{4-24}$ alkyl; and
the peptide includes from 2 to 50 amino acid residues.

In some embodiments, $R^{1C}$, $R^{2C}$, and $R^{3C}$ are each H.

In some embodiments, $R^{1C}$, $R^{2C}$, and $R^{3C}$ are each independently selected from H and $C_{1-4}$ alkyl.

In some embodiments, $R^1$, $R^2$, and $R^3$ are each independently selected from H and methyl.

In some embodiments, $R^1$ and $R^2$ are each H and $R^3$ is methyl.

In some embodiments, $L^{1C}$ is —C(O)NH—.

In some embodiments, the peptide includes from 2 to 20 amino acid residues (e.g., from 2 to 10 amino acid residues, from 5 to 10 amino acid residues).

In some embodiments, the core including a crosslinkable saccharide of Formulae (II-1) or (II-2) is configured to be crosslinked by exposure to ultraviolet light and a radical initiator. In some embodiments, the radical initiator is selected from anthraquinone-2-sulfonic acid sodium salt and 4,4-azobis(4-cyanovaleric acid). In some embodiments, the radical initiator is azobisisobutyronitrile. In certain embodiments, the radical initiator is a peroxide.

Additional Components

In some embodiments, the composition is a skin humectant. In some embodiments, the composition further includes a colorant, for example, titanium oxide and/or iron oxide. In some embodiments, the composition further includes a carrier (e.g., a lipophilic carrier such as mineral oil, oleic acid, etc.).

In some embodiments, the composition further includes a radical initiator, such as anthraquinone-2-sulfonic acid sodium salt or 4,4-azobis(4-cyanovaleric acid), in an amount of 0.01% or more (e.g., 0.05% or more, 0.1% or more, 0.3% or more, 0.5% or more, or 0.7% or more) and/or 1% or less (e.g., 0.7% or less, 0.5% or less, 0.3% or less, 0.1% or less, 0.05% or less) by mass.

In some embodiments, in addition to the aggregates above, the composition includes any number of additional components, such as, but not limited to: active ingredients (e.g., cosmetic, dermatological, and/or pharmaceutical), alcohols, allergy inhibitors, amino acids, anti-acne agents (e.g., salicylic acid), anti-aging agents, antiseptics, antifungal agents, antiperspirants, analgesics, anti-hair loss agents, anti-wrinkle agents, antibacterial agents, anti-microbial agents, anti-oxidants, anti-inflammatory agents, burn healing agents, colorants (e.g., lakes, pigments, and the like), de-pigmentation agents, deodorants, dyes, emollient (e.g., glycerin, butylene glycol), excipients, fatty substances, fillers, film formers (e.g., dimethicone acrylate copolymer, ethylhexyl acrylate copolymer), fragrances, free radical scavengers, glycerin, glycerin monostearate, glycerin distearate, hair growth agents, hair conditioners, hair softeners, hair moisturizers, herbal extracts, humectants (e.g., hyaluronic acid, orotic acid, lipoprotein), insect repellants, medication, moisturizers, non-active carrier oils (e.g., triglycerides, silicone oils, mineral oils), oils, peptides, polypeptides, proteins, perfumes, pigments, preservatives, plasticizers, reflectants, sebum absorbers, skin lightening agents, sunscreens, surfactants, tanning agents, thickening agents (e.g., hydroxyethylcellulose, xanthan gum, carbomer), Vaseline, vasoconstrictors, vasodilators, vitamins (e.g., Vitamin A, Vitamin E), water, waxes, and/or combinations thereof.

In some embodiments, the composition includes other cosmetic ingredients such as, but not limited to, humectants, emollients, moisturizers, anti-wrinkle ingredients, concealers, matte finishing agents, pigments, colorants, proteins, anti-oxidants, bronzers, chelating agents, emulsifiers, ultraviolet (UV) absorbing agents, oil absorbing agents, anti-foam agents, anti-tack agents, thickeners, fragrances, preservatives, anti-microbials, fungistats, neutralizing agents, vitamins, plasticizers, cohesion agents, basifying and acidifying agents, fillers, solvents, and/or mixtures thereof.

In some embodiments, the composition contains additional ingredients such as alkalinizing agents, emulsifying agents, emollients, plasticizers, preservatives, humectants, moisturizing agents, solvents, tonicity agents, active ingredients suitable to provide anti-aging benefits, and/or mixtures thereof. Examples of preferred additional ingredients include glycerin.

In some embodiments, additional ingredients are optionally added to the compositions as detailed below.

Colorants or pigments: In some embodiments, the composition includes one or more cosmetic powders, for example, calcium aluminum borosilicate, PMMA, polyethylene, polystyrene, methyl methacrylate crosspolymer, nylon-12, ethylene/acrylic acid copolymer, boron nitride, Teflon, silica, or the like. In some embodiments, the composition includes colorants or pigments to impart a desired color or effect, examples are inorganic pigments, organic pigments, and/or lakes. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Suitable inorganic pigments also include non-metal oxides such as alumina and silica, ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and the like. Organic pigments include, but are not limited to, at least one of carbon black, carmine, phthalocyanine blue and green pigment, diarylide yellow and orange pigments, and azo-type red and yellow pigments such as toluidine red, litho red, naphthol red and brown pigments, and combinations thereof.

"Lakes" generally refer to a colorant prepared from a water-soluble organic dye, (e.g., D&C or FD&C) which has been precipitated onto an insoluble reactive or adsorptive substrate or diluent. The term "D&C" as used herein means drug and cosmetic colorants that are approved for use in drugs and cosmetics by the FDA. The term "FD&C" as used herein means food, drug, and cosmetic colorants which are approved for use in foods, drugs, and cosmetics by the FDA. Certified D&C and FD&C colorants are listed in 21 C.F.R. § 74.101 et seq. and include the FD&C colors Blue 1, Blue 2, Green 3, Orange B, Citrus Red 2, Red 3, Red 4, Red 40, Yellow 5, Yellow 6, Blue 1, Blue 2, Orange B, Citrus Red 2, and the D&C colors Blue 4, Blue 9, Green 5, Green 6, Green 8, Orange 4, Orange 5, Orange 10, Orange 11, Red 6, Red 7, Red 17, Red 21, Red 22, Red 27, Red 28, Red 30, Red 31, Red 33, Red 34, Red 36, Red 39, Violet 2, Yellow 7, Yellow 8, Yellow 10, Yellow 11, Blue 4, Blue 6, Green 5, Green 6, Green 8, Orange 4, Orange 5, Orange 10, Orange 11, and so on. Substrates suitable for forming lakes include, without limitation, mica, bismuth oxychloride, sericite, alumina, aluminum, copper, bronze, silver, calcium, zirconium, barium, and strontium, titanated mica, fumed silica, spherical silica, polymethylmethacrylate (PMMA), micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, nylon, silica silylate, silk powder, sericite, soy flour, tin oxide, titanium hydroxide, trimagnesium phosphate, walnut shell powder, and mixtures thereof. Suitable lakes include, without limitation, those of red dyes from the monoazo, disazo, fluoran, xanthene, or indigoid families, such as Red 4, 6, 7, 17, 21, 22, 27, 28, 30, 31, 33, 34, 36, and Red 40; lakes of yellow pyrazole, monoazo, fluoran, xanthene, quinoline, dyes or salt thereof, such as Yellow 5, 6, 7, 8, 10, and 11; lakes of violet dyes including those from the anthroquinone family, such as Violet 2, as well as lakes of orange dyes, including Orange 4, 5, 10, 11, and the like. Suitable lakes of D&C and FD&C dyes are defined in 21 C.F.R. § 82.51.

In some embodiments, the coloring agents are optionally surface treated, for example, to make the coloring agents more hydrophobic or more dispersible in a vehicle. In one embodiment, the surface of the coloring agents is, for example, covalently or ionically bound to an organic molecule or silicon-based molecule or is adsorbed thereto, or the coloring agents is physically coated with a layer of material. In certain embodiments, the surface treatment compound is attached to the coloring agents through any suitable coupling agent, linker group, or functional group (e.g., silane, ester, ether, etc). In some embodiments, the compound includes a hydrophobic portion which is selected from, for example, alkyl, aryl, allyl, vinyl, alkyl-aryl, aryl-alkyl, organosilicone, di-organosilicone, dimethicones, methicones, polyurethanes, silicone-polyurethanes, and fluoro- or perfluoro-derivatives thereof. Other hydrophobic modifiers include lauroyl lysine, isopropyl titanium triisostearate (ITT), ITT and dimethicone (ITT/dimethicone) cross-polymers, ITT and amino acid, ITT/triethoxycaprylylsilane crosspolymer, waxes (e.g., camauba), fatty acids (e.g., stearates), HDI/trimethylol hexylactone crosspolymer, PEG-8 methyl ether triethoxysilane, aloe, jojoba ester, lecithin, perfluoroalcohol phosphate, and Magnesium Myristate (MM), to name a few.

In some embodiments, a pigment component includes an alkyl silane surface-treated colorant including an alumina substrate (e.g., platelet shaped) and a pigment, dye, or lake bonded to the alumina substrate by an alkyl silane surface treatment. In some embodiments, the alkyl silane is octylsilane, and is formed by treatment with triethoxy caprylylsilane. Non-limiting examples of such colorants include, but are not limited to, alumina/titanium dioxide/triethoxycaprylylsilane 1% (COVALUMINE™ Atlas White AS), alumina/D&C Red aluminum lake CTD/Triethoxycaprylylsilane 1% (COVALUMINE™ Red Rose AS), alumina/D&C red aluminum lake CTD/triethoxycaprylylsilane 1% (COVALUMINE™ Sonoma Red AS), alumina/black iron oxide CTD/triethoxycaprylylsilane 1% (COVALUMINE™ Sonoma Black AS), alumina/D&C red #6 aluminum lake CTD/triethoxycaprylylsilane 1% (COVALUMINE™ Fire Red AS), alumina/yellow iron oxide CTD/triethoxycaprylylsilane 1% (COVALUMINE™ sonoma yellow AS), alumina/D&C blue #1 aluminum lake CTD/triethoxycaprylylsilane 1% (COVALUMINE™ Astral Blue AS), alumina/carmine CTD/triethoxycaprylylsilane 1% (COVALUMINE™ Campari AS), alumina/yellow #5 CTD/triethoxycaprylylsilane 1% (COVALUMINE™ Sunburst AS), alumina/triethoxycaprylylsilane 1%, and combinations thereof, each of which is available from SENSIENT™ CosmeticTechnologies LCW.

In some embodiments, interference or pearl pigments are included in the composition. Interference or pearl pigments typically are formed of micas layered with about 50 to 300 nm films of $TiO_2$, $Fe_2O_3$, or $Cr_2O_3$ or the like. These include white nacreous materials, such as mica covered with titanium oxide or covered with bismuth oxychloride; and colored nacreous materials, such as titanium mica with iron oxides, titanium mica with ferric blue or chromium oxide, titanium mica with an organic pigment of the aforementioned type. In some embodiments, interference or pearl pigments are used collectively in an amount of less than 1.0 wt %. In some embodiments, the pearlescent component has a bismuth oxychloride based pearlescent ingredient or reflectance pearls. It is believed that bismuth oxychloride matches the skin's natural pearlescence more than compounds such as titanium oxide. However, other pearlescent ingredients may be used. In some embodiments, the pearlescent component is CHROMA-LITE, which is a combination of colored pigment bonded to BI-LITE 20 (bismuth oxychloride and mica) using calcium stearate.

In some embodiments, the composition includes cosmetically acceptable vehicles. In some embodiments, the vehicle includes a liquid, including a single phase, a dual-phase system, or an emulsion. Emulsions include oil-in-water, silicone-in-water, water-in-oil, water-in-silicone, and the like. When formulated as an emulsion, an emulsifier is typically included. Examples of cosmetically acceptable vehicles include volatile silicones (e.g., cyclopentasiloxane), hydrocarbons, ester oils, lower alcohols (e.g., ethanol, isopropyl alcohol, etc.), and water.

In some embodiments, the composition includes emollients. Examples of emollients include, but are not limited to, esters oils (e.g., the etherification product of an acid of the form $R^A(COOH)_{1-2}$ with an alcohol of the form $R^B(OH)_{1-3}$ where $R^A$ and $R^B$ are each independently linear, branched, or cyclic hydrocarbon groups, optionally containing unsaturated bonds, and having from 1 to 30 carbon atoms, preferably from 2 to 30 carbon atoms, and more preferably, from 3 to 30 carbon atoms, optionally substituted with one or more functionalities including hydroxyl, oxa, oxo, and the like. In some embodiments, at least one of $R^A$ and $R^B$ includes at least one aliphatic chain. The esters defined above include, without limitation, the esters of mono-acids with mono-alcohols, mono-acids with diols and triols, di-acids with mono-alcohols, and tri-acids with mono-alcohols. Other emollients include dimethicone. In some embodiments, humectants, such as glycerin and other C1-10 polyols or diols are also included.

In some embodiments, the composition includes fillers in an amount from about 1% to about 20% (e.g., from about 1% to about 10%) by weight of the final composition. Examples of fillers include, but are not limited to, silica, PMMA, nylon, alumina, barium sulfate, or any other filler typically used in such compositions.

In some embodiments, the composition includes film formers. Examples of polymeric film formers include cellulosics, polyolefins, polyvinyls, polyacrylates, polyurethanes, silicones, silicone acrylates, polyamides, polyesters, fluoropolymers, polyethers, polyacetates, polycarbonates, polyimides, rubbers, epoxies, formaldehyde resins, and homopolymers and copolymers of any of the foregoing.

In some embodiments, the composition includes oils. Suitable non-limiting examples of oils for the oil phase (for example, in an emulsion) include natural and synthetic oils, including animal, vegetable, and petroleum oils; fatty acid triglycerides; fatty acid esters such as octyl palmitate, isopropyl myristate and isopropyl palmitate; ethers such as dicapryl ether; fatty alcohols such as cetyl alcohol, stearyl alcohol and behenyl alcohol; sterols; hydrocarbons such as isooctane, isododecane, isohexadecane, decane, dodecane, tetradecane, tridecane, $C_{8-20}$ isoparaffins, mineral oil, petrolatum, isoeicosane and polyisobutene; $C_{10-30}$ cholesterol/lanosterol esters; lanolin; and the like. Representative hydrocarbons include paraffinic hydrocarbons available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename PERMETHYL 99A™ are also contemplated to be suitable. Various commercially available $C_{16}$ isoparaffins, such as isohexadecane (having the tradename PERMETHYL®) are also suitable. In some embodiments, silicone oils such as dimethicones, cyclic silicones, and polysiloxanes may also be included in the oil phase. In one embodiment, silicone oils are present in an amount less than about 5% by weight of the oil phase.

In some embodiments, the composition includes thickeners. Examples of suspending and thickening agents include silica gels, gums, clays, fumed silica, fatty acid soaps, and various hydrocarbon gels, and other ingredients that when incorporated into the formulation remain on the surface of keratinous tissues as disclosed in the *International Cosmetic Dictionary and Handbook* (12th Ed.), which is hereby incorporated by reference. In some embodiments, the composition includes viscosifying agents such as gellants. Examples of viscosifying agents include bentone, triglycerides, aluminum stearate, $C_{18}$-$C_{36}$ acid glycol esters, glyceryl tribehenate, glycerol monostearate, alginates, carbomers, celluloses, gums, carageenans, starches or silicates.

In some embodiments, the composition includes waxes. Examples of waxes include, but are not limited to, linear polyethylene, microcrystalline petroleum wax, carnauba wax, lignite wax, ouricouri wax, rice bran wax, castor wax, mortar wax, stearone, acrawax, bayberry wax, castor wax, Japan wax, ozokerite, beeswax, candelilla wax, petrolatum, ceresin wax, cocoa butter, illipe butter, esparto wax, shellac wax, ethylene glycol diesters or triesters of $C_{18}$-$C_{36}$ fatty acids, cetyl palmitate, paraffin wax, hard tallow, lanolin, lanolin alcohol, cetyl alcohol, glyceryl monostearate, sugarcane wax, jojoba wax, stearyl alcohol, silicone waxes, and combinations thereof.

It is understood to those skilled in the art that any other cosmetically acceptable ingredients, i.e., those included in the *CFTA Cosmetic Ingredient Dictionary*, 3rd Ed., may be used.

Synthesis of Compounds (I-1), (I-2), (II-1), and (II-2)

The novel compounds of the present disclosure can be prepared in a variety of ways known to one skilled in the art of organic synthesis. The compounds of the present disclosure can be synthesized using the methods as hereinafter described below, together with synthetic methods known in the art of synthetic organic chemistry or variations thereon as appreciated by those skilled in the art.

The compounds of this disclosure can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 4th. Ed., Wiley & Sons, 2006, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

The compounds of the disclosure can be prepared, for example, using the reaction pathways and techniques as described below.

Figure 4:
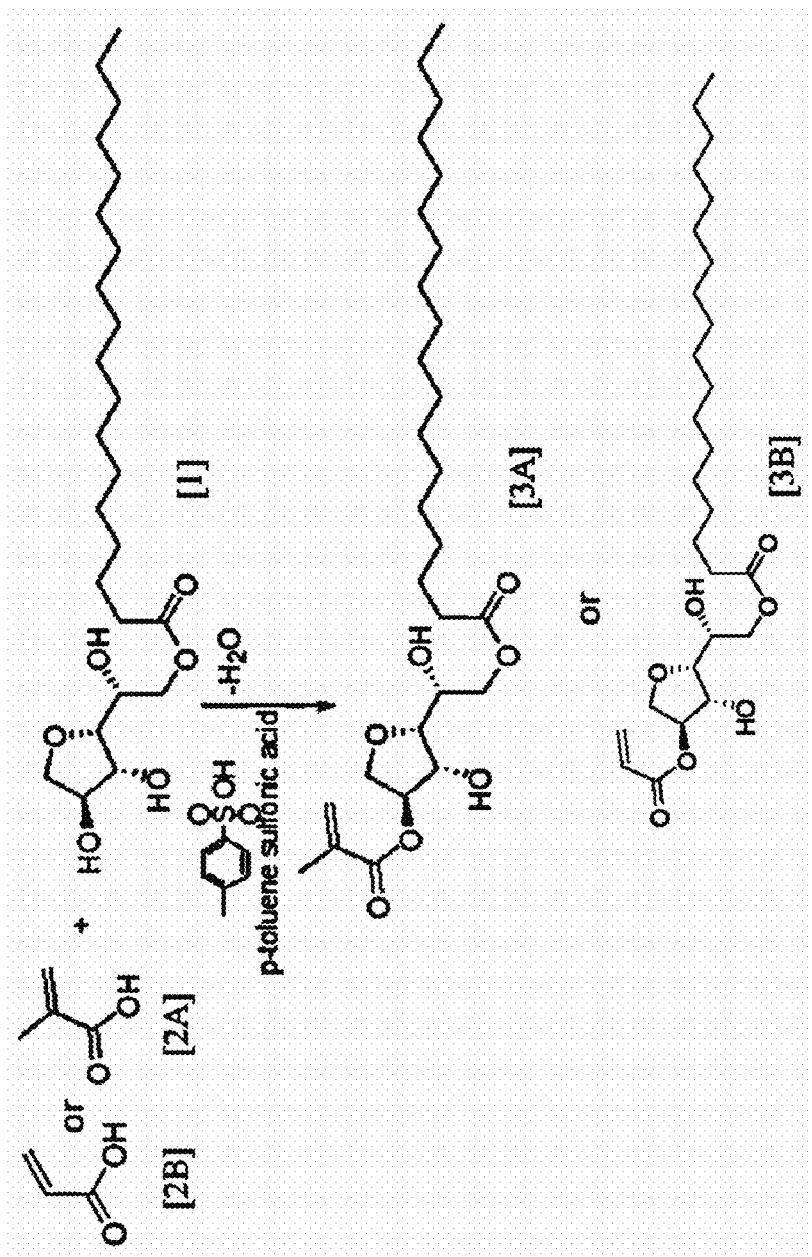
FIG. 4 is a scheme showing the synthesis of embodiments of aggregate-forming compounds of the present disclosure.
Figure 7:
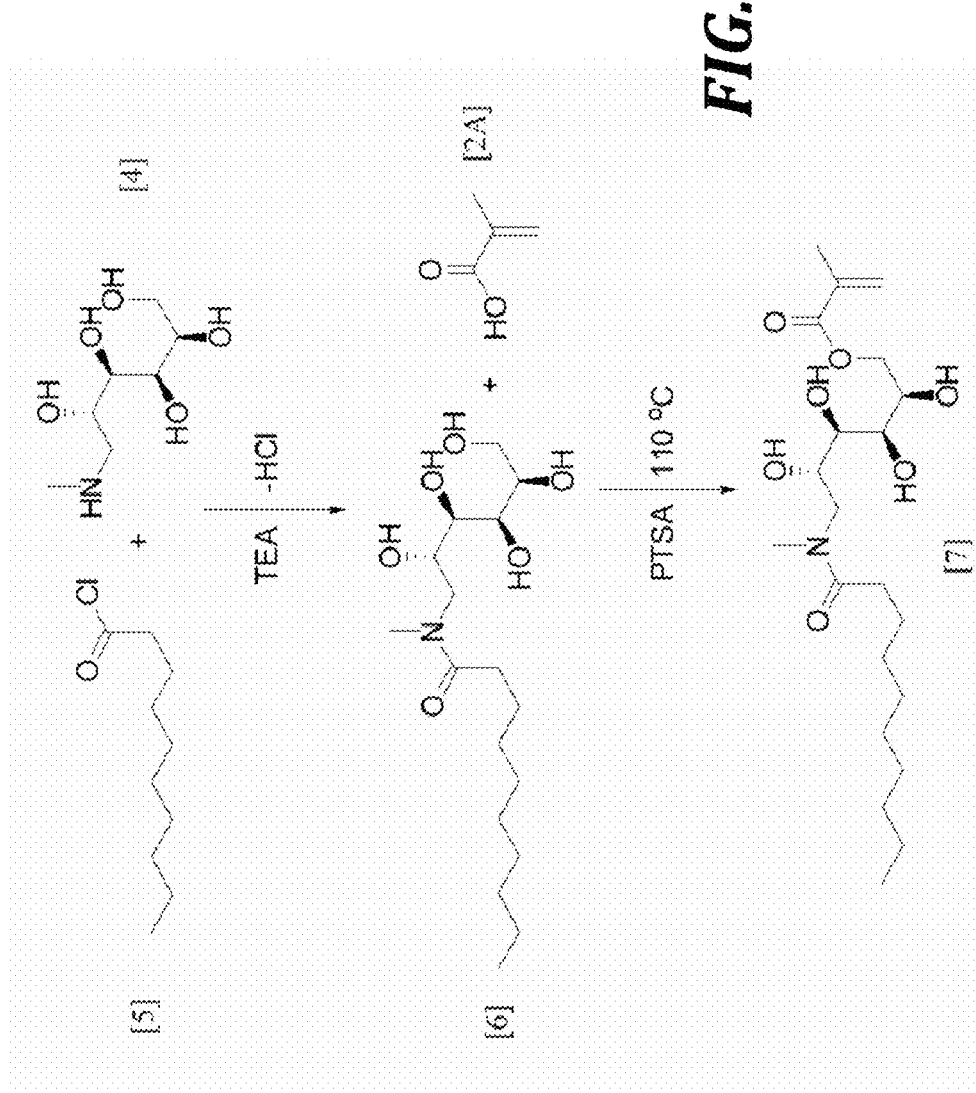
FIG. 7 is a scheme showing the synthesis of an embodiment of aggregate-forming compounds of present disclosure.
Figure 8:
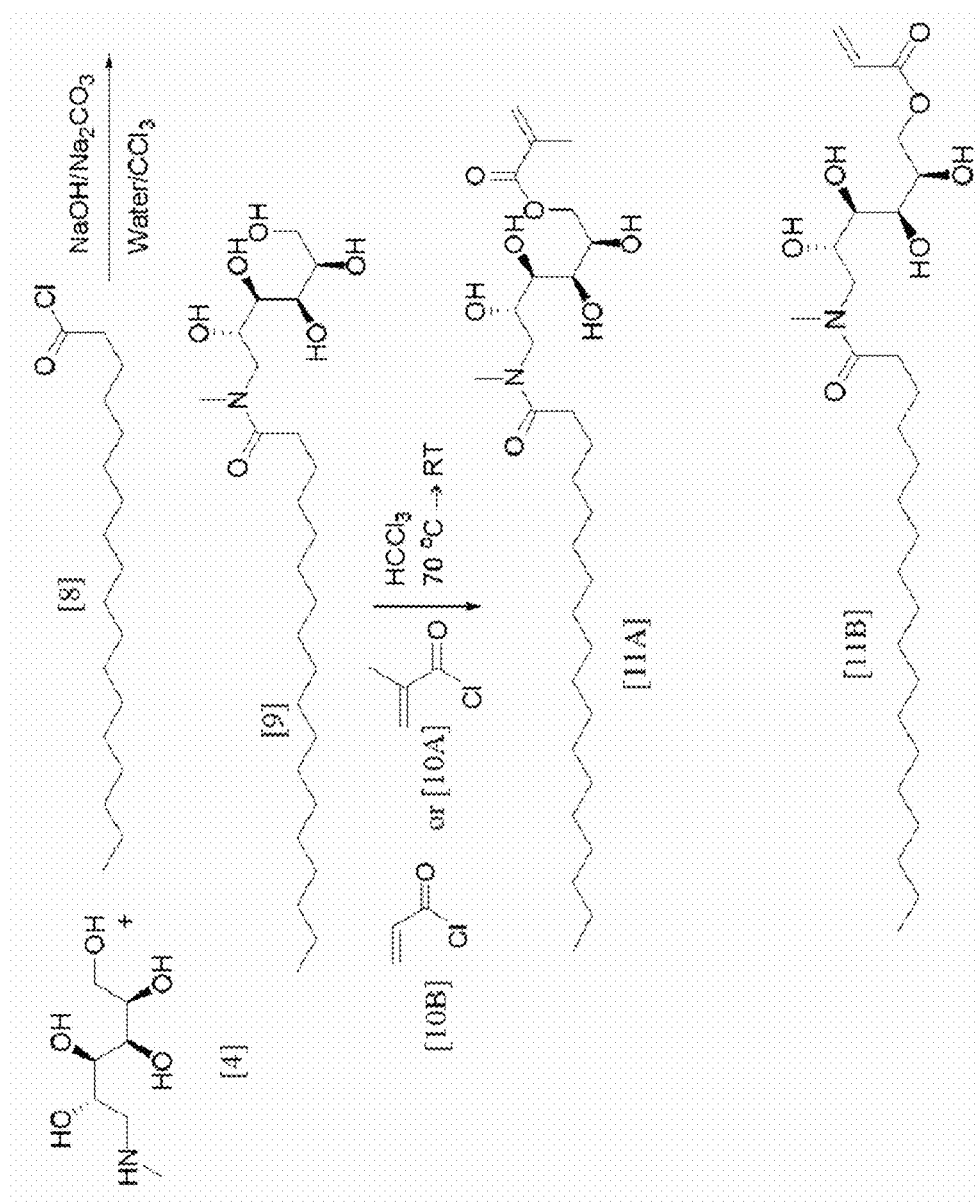
FIG. 8 is a scheme showing the synthesis of embodiments of aggregate-forming compounds of the present disclosure.

In general, a compound of Formulas (I-1), (I-2), (II-1), or (II-2) is synthesized by reacting a reactive group (e.g., a hydroxyl, a carboxylic acid, an amine, etc.) on a saccharide, polysaccharide, amino acid, polyamino acid, etc., with a fatty acid derivative (e.g., fatty acid, fatty acid chloride, activated fatty acid) to form a saccharide, polysaccharide, amino acid, or polyamino acid that is covalently bonded to an alkyl chain. A reactive group on the product is then reacted with an acrylic acid derivative (e.g., acrylic acid, methacrylic acid, substituted acrylic acids, acryloyl chloride, methacryloyl chloride, substituted acryloyl chlorides, etc.) to form a compound of Formulas (I-1), (I-2), (II-1), (II-2) having a crosslinkable vinyl group. In some embodiments, reaction of the saccharide, polysaccharide, amino acid, polyamino acid, etc., with the acrylic acid derivative occurs before, or concurrently with, reaction with the fatty acid derivative. Examples of compound synthesis are illustrated in FIG. 4, FIG. 7, FIG. 8, and in Examples 1 and 2, below.

In some embodiments, the reaction of the saccharide, polysaccharide, amino acid, polyamino acid, etc., with the fatty acid derivative and/or the acrylic acid derivative is catalyzed (e.g., by an acid, such as tosylic acid; or a base, such as triethylamine; or otherwise catalyzed). In some embodiments, the acrylic acid derivative and/or or the fatty acid derivative is activated, for example, by formation of an N-hydroxysuccinimide ester (e.g., acrylic acid N-hydroxysuccinimide ester, substituted acrylic acid N-hydroxysuccinimide ester, or fatty acid N-hydroxysuccinimide ester). In some embodiments, the reaction between the saccharide derivative, polysaccharide derivative, amino acid derivative and the acrylic acid derivative and/or the fatty acid derivative is mediated by a coupling agent (e.g., carbodiimides).

The compound of Formulas (I-1) and (I-2) are crosslinked to provide a polymer of Formulas (I), (I-A), (I-B), (I-C), or (I-D); and the compound of Formulas (II-1) and (II-2) are crosslinked to provide a polymer of Formulas (II) by exposure to ultraviolet light in the presence of a radical initiator, as discussed above. In some embodiments, a compound of Formula (I-E) or (II-A) is formed when the compound of Formula (I-1) and (I-2), or the compound of Formula (II-1) and (II-2), respectively, is exposed to ultraviolet light in the presence of a radical initiator.

Assembly of Aggregates

In some embodiments, the polysaccharide aggregates are formed by equilibrium micelle formation in oil and water solutions or by formation of colloids in an oil-water emulsion.

Figure 3:
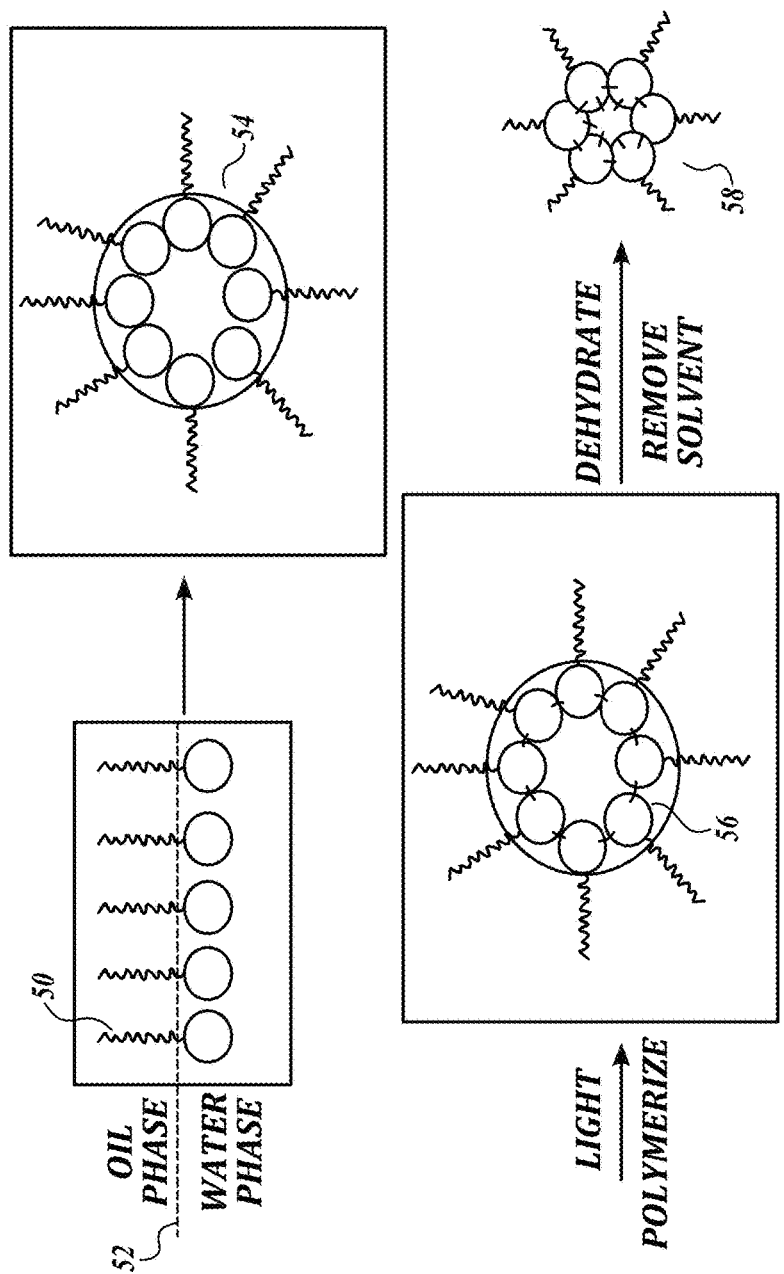
FIG. 3 is a schematic representation of an assembly and formation of an embodiment of aggregates of the present disclosure.

The formation of reverse micelles and the crosslinking of the molecules forming the micelle are shown in FIG. 3, where an amphiphile 50 at an oil-water interface 52 self-assembles into a reverse micelle 54. Following exposure to light, the core of the reverse micelle is crosslinked to form a permanent reverse micelle 56, which is then dehydrated to form a dry aggregate 58 that can be acoustically activated to absorb water.

Prior to water absorption, in some embodiments, the aggregates have an initial diameter of 5 nm or greater (e.g., 6 nm or greater, 7 nm or greater, or 8 nm or greater) and/or 10 nm or less (e.g., 8 nm or less, 7 nm or less, or 6 nm or less). After water absorption, in some embodiments, the aggregates have a final diameter of 12 nm or greater (e.g., 15 nm or greater, or 17 nm or greater) and/or 20 nm or less (e.g., 17 nm or less, or 15 nm or less). In some embodiments, an aggregate diameter is measured using dynamic light scattering when the aggregate is in vitro. In certain embodiments, an aggregate diameter is measured using microscopic histology when the aggregate is in vivo.

Methods of Use

In some embodiments, to hydrate a skin portion, the composition including the activatable aggregate is applied to a skin portion and the aggregate is absorbed into an epidermal layer of the skin portion to provide an absorbed aggregate. The core of the absorbed aggregate in the epidermal layer is then swelled by applying an acoustic energy sufficient to allow the core to absorb water from the epidermis to provide a swollen absorbed aggregate. In some embodiments, the acoustic energy is from 1 kilohertz (kHz) to 100 megahertz (MHz) (e.g., 1 kHz to 60 MHz).

In some embodiments, swelling the core of the absorbed aggregate in the epidermal layer includes applying an acoustic stimulus of a character and for a duration sufficient to allow the permeation of neighboring water molecules in the epidermis through a shell of the absorbed aggregate and into the core. In some embodiments, the permeability a shell of the absorbed aggregate in the epidermal layer is varied by applying an acoustic stimulus of a character and for a duration. In some embodiments, swelling the core of the absorbed aggregate in the epidermal layer includes sequestering neighboring water molecules (e.g., into the core of the absorbed aggregate) in the presence of an applied acoustic stimulus.

In some embodiments, the acoustic stimulus is applied to a skin portion for a duration of 1 second or more (e.g., 5 seconds or more, 10 seconds or more, 30 seconds or more, 1 minute or more, 5 minutes or more, 10 minutes or more, or 20 minutes or more) and/or 30 minutes or less (e.g., 20 minutes or less, 10 minutes or less, 5 minutes or less, 1 minute or less, 30 seconds or less, 10 seconds or less, or 5 seconds or less).

In some embodiments, the cosmetic compositions disclosed herein is applied to one or more skin surfaces and/or one or more mammalian keratinous tissue surfaces as part of a user's daily routine or regimen. In some embodiments, the composition is used on an "as needed" basis. In some examples, an effective amount of the cosmetic composition is applied to a target portion of the keratinous tissue or skin.

In some embodiments, the method includes a step identifying a skin surface for treatment with the cosmetic composition for improving skin condition. In some embodiments, the skin surface is identified by the user or a third party such as a dermatologist, cosmetician, or other individual, or even by a combination of different individuals. Identification may be done, for example, by visual inspection of the skin surface in need of treatment.

In some embodiments, skin surfaces suitable for application of the composition include those not typically covered by clothing such as facial skin surfaces, hand and arm skin surfaces, foot and leg skin surfaces, and neck and chest skin surfaces (e.g., décolletage). For example, areas identified for application may include areas such as the forehead, perioral, chin, periorbital, nose, and/or cheek skin surfaces. In another example, the composition is applied to any facial skin care surface and/or any other skin surface identified as in need of treatment by the cosmetic composition.

In some embodiments, the method includes a step of applying the composition to the skin surface, which may or may not have been previously identified. Many regimens exist for the application of the composition. In some embodiments, the composition is applied as needed and/or at least once a day, twice a day, or on a more frequent daily basis. In some embodiments, the composition is applied over a period of, for example, between about 1 week and about 12 weeks, between about 4 weeks and about 12 weeks, and/or between about 4 weeks and about 8 weeks, over multiple months (i.e., 3-12 months) or multiple years. In some embodiments, when applied twice daily, the first and second applications are separated by at least 1 to about 12 hours. For example, the cosmetic composition is applied in the morning and/or in the evening before bed.

The following examples are provided to illustrate, not limit, the disclosure.

EXAMPLES

Permanent reverse micelles were synthesized by covalently crosslinking the core of a reverse micelle. Specifically, an amphiphilic molecule was functionalized with a photo-reactive vinyl on its hydrophilic head group, assembled into a reverse micelle, then crosslinked. In general, the sequence of synthetic steps includes (1) selection or synthesis of a large head-group amphiphile, (2) functionalization with a photo-labile moiety, (3) formation of reverse micelles from molecules in a non-polar phase, and (4) exposure to UV light to induce crosslinking.

Example 1. Permanent Reverse Micelles with Crosslinked Saccharide Cores

Referring to FIG. 4, sorbitan monostearate [1] was selected as the amphiphile and it was esterified with acrylic acid [2B] or methacrylic acid [2A] to form a photo-crosslinkable molecule [3B] or [3A], respectively, that is capable of forming a reverse micelle.

Specifically, sorbitan monostearate at 4.457 g (10.4 mmol) was added to a 20 mL vial. To this vial was added a small stir bar followed by 10.000 g (116.2 mmol) of (meth) acrylic acid, 0.050 g of p-toluene sulfonic acid, and 6.000 g of calcium chloride (anhydrous). The calcium chloride absorbed water formed by the reaction. The vial was sealed shut and heated on an oil bath to 110-120° C. for three hours. During the reaction progress the calcium chloride clumped together and then eventually became a powder. After three hours the (meth)acrylic acid solution was poured into hot water. The waxy product [3A] floated to the top of the water. When cooled to room temperature, the waxy product solidified. The solid material was washed with water and allowed to dry. The waxy material was soluble in hot chloroform but formed cloudy solutions at room temperature. The $^1$H NMR was taken in chloroform. This reaction yielded 4.532 g (87%) of product [3A]. A similar reaction was conducted using acrylic acid [2A] yielding [3B] and proton NMR was obtained.

Figure 5:
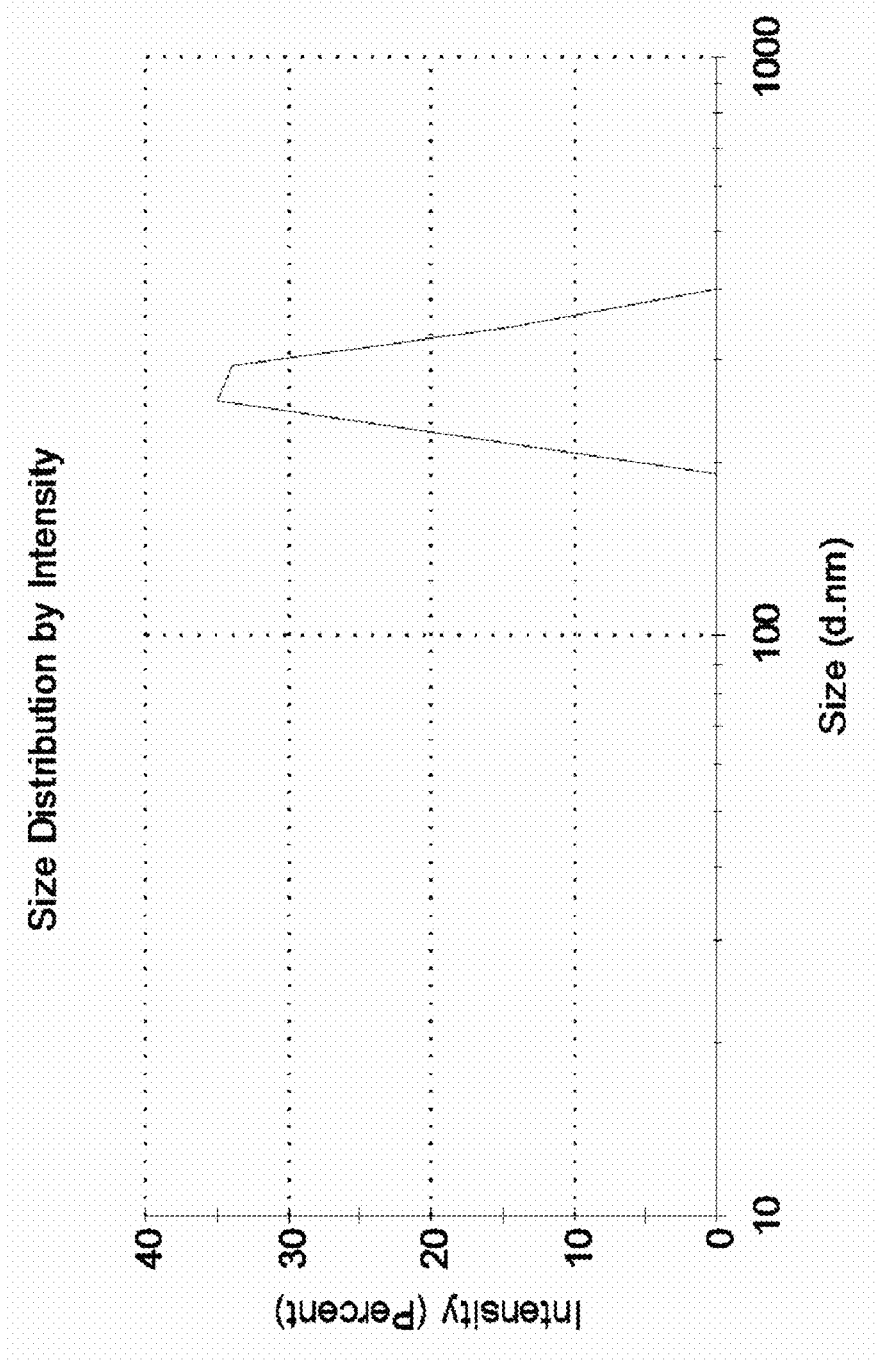
FIG. 5 is graph showing dynamic light scattering (DLS) results of an embodiment of aggregates of the present disclosure.

To form reverse micelles of [3B] in a non-polar solvent, 4.5 g of acryloyloxy-sorbitan monostearate was added to 500 mL of xylenes under an argon atmosphere with an argon inlet. The xylenes were heated to 65° C. to aid dissolution. The solution was agitated with a high speed mixer set to 3000 rpm. The solution was allowed to cool back to room temperature and remained clear. A photo-initiator solution of 80 mg of anthraquinone-2-sulfonic acid sodium salt was created in 2 mL of de-ionized water. While agitated at 17,000 rpm with the same mixer this water photo-sensitizer solution was then added drop wise to the xylenes. The solution went from clear to an opaque white. The solution was then irradiated with a 400 nm lamp for 4 hours. The solution became warm and the water evaporated out of the solution and flushed off by the argon. The solution changed from an opaque white to clear. Referring to FIG. 5, the dispersion was then characterized by Dynamic Light Scattering (DLS) and the average aggregate size was measured to be 276 nm with a standard deviation of 38 nm.

Figure 6:
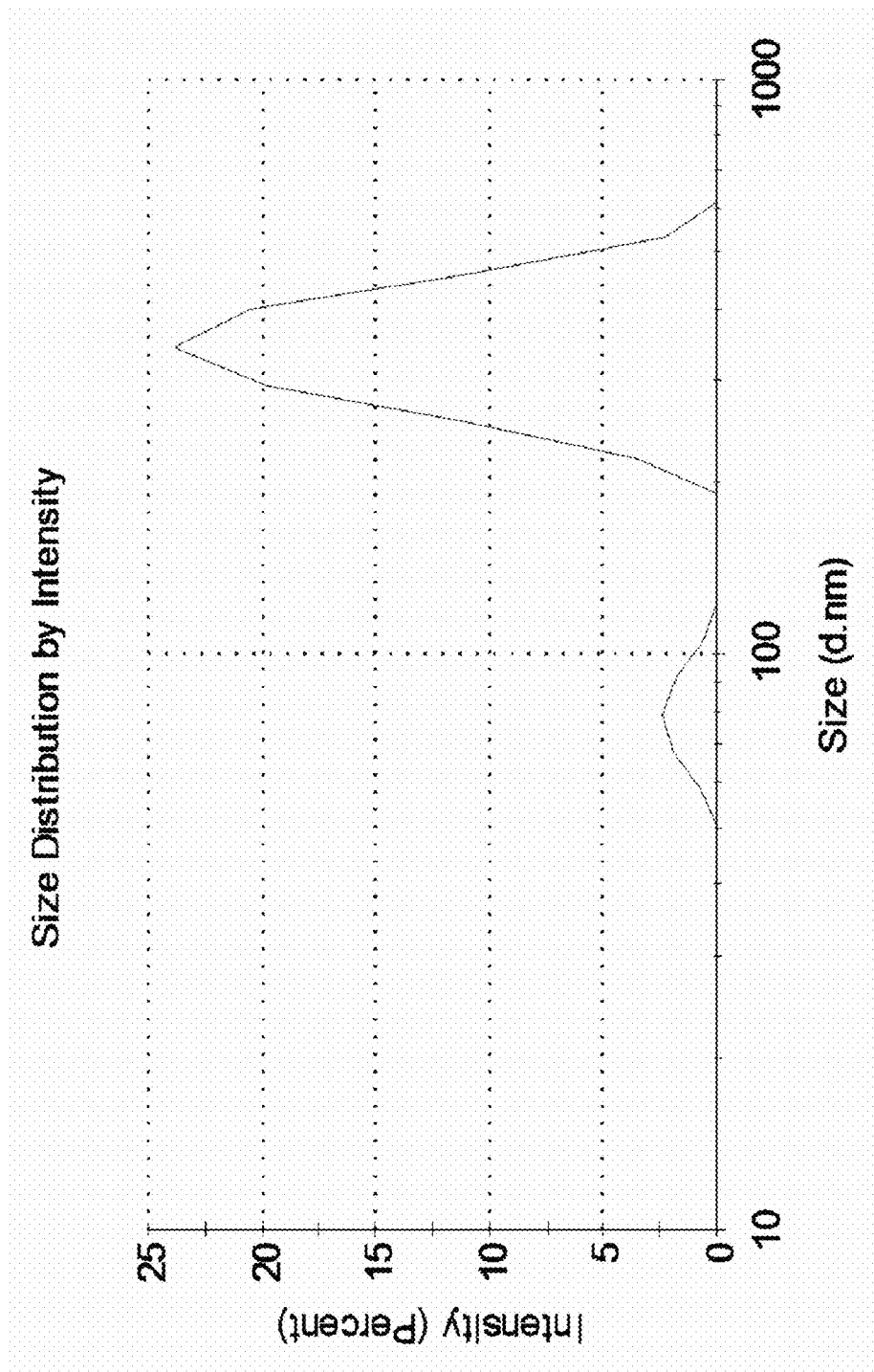
FIG. 6 is a graph showing dynamic light scatter (DLS) results of an embodiment of aggregates of the present disclosure.

Another run of this same experiment was conducted but with the addition of a different solution at the 17,000 rpm step—namely a photo-initiator solution of 240 mg of anthraquinone-2-sulfonic acid sodium salt in 6 mL deionized water and 2 mL glycerol. This water-glycerol photo-sensitizer solution was then added drop wise to the xylenes to a total of 2 mL. The xylenes changed from clear to an opaque white upon the addition of the water-glycerol solution. The xylenes phase was then irradiated with a 400 nm lamp for 4 hours. The solution became warm and the water was evaporated out of the solution and flushed off by the argon. The solution changed from an opaque white to clear. Referring to FIG. 6, dynamic Light Scattering revealed a bimodal aggregate size distribution at 80 nm with a standard deviation of 13 nm and 350 nm with a standard deviation of 72 nm.

Example 2. Permanent Reverse Micelles with Crosslinked Amino Acid Cores

Functionalized reverse micelles were synthesized using a glucamine peptide moiety for the hydrophilic head group—where an acyl chloride amine reaction attaches a hydrophilic tail and an acrylic ester provides a photo-labile cross-linker.

Referring to FIG. 7, N-methyl-D-glucamine [4] was dispersed into water and sodium hydroxide at room temperature. Decanoyl chloride [5] is then added to the N-methyl-D-glucamine solution and the two are stirred together for two hours. Calcium chloride is added to the solution which causes the product N-decanoyl-N-methyl-D-glucamine [6] to separate. The compound [6] is extracted using chloroform which is dried over calcium chloride and removed by rotary evaporation. The resulting N-decanoyl-N-methyl-D-glucamine [6] was dissolved into methacrylic acid [2A] (2.5 g compound to 10 mL of methacrylic acid). Calcium chloride was added to the solution to absorb water as it is formed by ester formation. The methacrylic acid solution was then heated to 110-120° C. for three hours. Proton NMR was obtained and confirms product [7].

Referring to FIG. 8, a similar reaction was performed where 32 g of N-methyl-D-glucamine [4] was dissolved into 100 mL of water with 8 grams of sodium hydroxide and 5 grams of sodium carbonate. Then 25 g of stearoyl chloride [8] was melted and added to chloroform. Both the water and chloroform solutions were cooled on ice. The chloroform solution was then slowly added to the water phase. A white, waxy precipitate [9]quickly formed. The reaction was stirred for two hours after which the waxy precipitate was washed with a large amount of water. The solid was allowed to dry and then crushed. The finely divided grains were washed further with water and dried. Proton NMR was obtained and confirms product [9].

The dried product [9] (5 g) was then added to 150 mL of anhydrous chloroform under dry air. The system was heated to 70° C. and was slightly cloudy. To this solution was added 1.5 g of triethylamine. To the heated chloroform was added using dropwise addition 1.25 equivalents (~1.1 g) methacryloyl chloride [10A] or acryloyl chloride [10B] over a period of 15 minutes. The system largely became clear when the addition was complete. The chloroform was then added to ~300 ml of water and shaken. The resulting emulsion was then placed on a rotary evaporator to remove excess organics and solvent. The result was a white, colorless precipitate in water. To the water was added ~10 g of a saturated sodium carbonate water solution and heated to 70-75° C. The resulting system was then filtered, washed with sodium carbonate solution and then with a large amount of de-ionized water. The solid material [11A] or [11B] was air dried then vacuum dried. The respective proton NMR for methacryloyl [11A] and acryloyl [11B] products were obtained and confirms the products.

To form reverse micelles of the glucamine-stearate amphiphiles, 4.5 g of the acryloyloxy-N-methyl-N-stearoyl-D-glucamine [11B] was added to 500 mL of xylenes under an argon atmosphere with an argon inlet. The xylenes were heated to 65° C. to increase dissolution. The solution was dispersed with a high shear mixer at 3000 rpm. The solution was allowed to cool back to room temperature and remained clear. A photo-initiator solution of 80 mg of anthraquinone-2-sulfonic acid sodium salt was created in 2 mL of de-ionized water. This solution was then added drop wise to the xylenes while dispersed at 17,000 rpm by the high shear mixer. The solution went from clear to an opaque white. The solution was then irradiated with a 400 nm lamp for 4 hours. The solution became warm and the water evaporated out of the solution and was flushed out by the argon. The solution changed from an opaque white to clear.

Dynamic light scattering was performed on this dispersion and the average aggregate size was measured to be 76 nm with a standard deviation of 17 nm.

A similar run of the experiment above was conducted, where at the 17,000 rpm mixing step, a solution of 100 mg of 4,4-azobis(4-cyanovaleric acid) in 2 mL of de-ionized water (with 50 mg of sodium carbonate) was added. Again the water solution was then added drop wise to the xylenes at room temperature. The solution went from clear to an opaque white. The solution was then heated to 90° C. for 3 hours 45 minutes. The solution changed from an opaque white to clear during the process. Dynamic Light Scattering showed the average aggregate size to be bimodal at 78 nm with a standard deviation of 18 nm and 339 nm with a standard deviation of 148 nm.

Example 3. Polysaccharide Hydrogel-Based Aggregates

Aggregates were synthesized using hydroxyethylcellulose (HEC) functionalized with an acoustically sensitive hydrophobic layer.

Many naturally occurring oils contain unsaturated $C_{18}$ chains, such as oleic, linoleic or linolenic acid. The saturated $C_{14}$ to $C_{18}$ chains of fatty acids such palmitic acid, myristic acid undergo molecular ordering and stacking that in turn exhibit distinct crystallization properties and higher melting points compared to unsaturated fatty acids. This hydrocarbon packing of linear aliphatics can generate robust hydrophobic shells around HEC gels. The HEC serves as a hydrophilic core and the fatty acid chains form a hydrophobic and molecularly ordered shell around the core. Here, as shown in Scheme 1, above, both the backbone and the grafts of HEC are covered in hydroxyl moieties serve as reactive points to attach a hydrophobic shell about a HEC core. Functional groups such as carboxylic acids or acyl chlorides can react to attach the hydrophobic layer. Alternatively, alkyl isocyanates are used to produce urethane linkages, resulting in hydrophobic modified HEC colloids.

Figure 9:
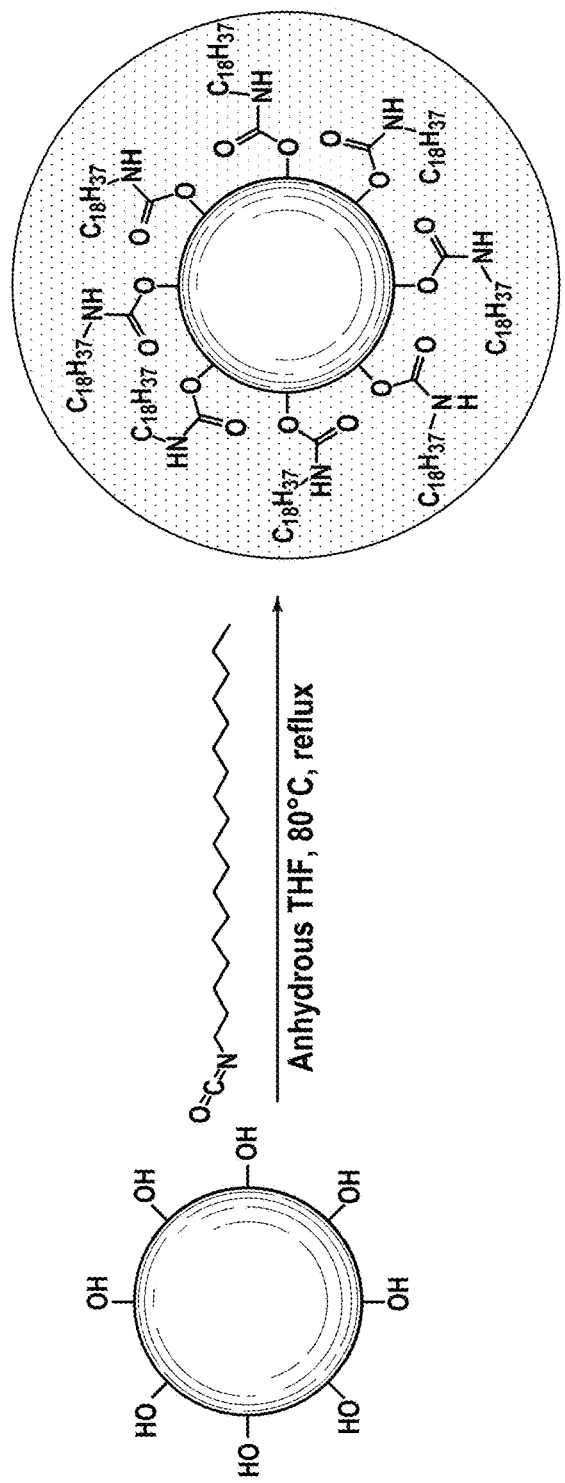
FIG. 9 is a schematic representation of an embodiment of aggregates of the present disclosure.

A number of alkyl chain lengths were explored. FIG. 9 shows the general reaction scheme for the reaction of an alkyl isocyanate with a HEC, where an aggregate having a shell of aliphatic chain is finally generated. Table 1 shows the solubility results of alkyl-functionalized HEC, synthesized using various alkyl isocyanates and different ratios relative to the HEC.

TABLE 1

Summary of alkyl isocyanate reactions with HEC.

| Alkyl isocyanate | HEC (g) | Alkyl (g) | Mole Ratio alkyl:HEC | Solubility $H_2O$ |
|---|---|---|---|---|
| butyl | 10.9 | 0.8 | 1:4.0 | Soluble |
| butyl | 10.6 | 0.5 | 1:14.5 | Soluble |
| octyl | 11.1 | 0.8 | 1:22.0 | Soluble |
| octyl | 10.4 | 1.2 | 1:6.6 | Translucent |
| octyl | 100.0 | 25.0 | 1:0.8 | Insoluble |
| dodecyl | 10.9 | 1.0 | 1:34.0 | Soluble |
| dodecyl | 11.4 | 1.2 | 1:10.0 | Translucent |
| dodecyl | 11.2 | 2.2 | 1:6.0 | Insoluble |
| stearyl | 10.9 | 1.7 | 1:12.0 | Insoluble |
| stearyl | 9.8 | 1.5 | 1:6.0 | Insoluble |
| stearyl | 10.2 | 2.0 | 1:2.0 | Insoluble |
| stearyl | 284.0 | 100.0 | 1:1.5 | Insoluble |

For a stearyl isocyanate-functionalized HEC, the thickness of a dense C18 layer (using C—C bond lengths of 1.55 Å and the bond angles is 109°) was estimated to be a 2.5 nm thick layer. Thus, a HEC phase was calculated to have ~5 nm thick hydrophobic shell imparted by the C18 chain.

High Ratio Octadecyl Functionalized HEC

A 2 L heavy wall glass flask was flamed dried and flooded with argon. To the flask was added a Dean-Stark trap, condenser, and a stirring rod. To the flask was added 284.0 g of hydroxyethylcellulose (Ashland Chemical, LOT#20363) followed by 550 mL of toluene. The stir rod was connected to the motor and the system was stirred under argon atmosphere. The temperature was raised until a strong reflux resulted. The toluene was refluxed for 6 hours during which ~46 mL of water was removed.

The reaction was then cooled to ~80° C. and dibutyltin dilaurate (0.2 g, 0.3 mmol, Aldrich LOT#MKBK0920V) was added by syringe followed by 100.0 g of octadecyl isocyanate (technical grade, 338.4 mmol, Aldrich LOT #MKBP2687V). The system was heated to 90-95° C. for 12 hours followed by 105-110° C. for 4 hours. The toluene became very viscous. The system was then cooled to 60° C., added to ~500 mL of acetone, mixed, and allowed to sit for 30 minutes. The acetone/toluene was decanted and 1 L more acetone added, mixed, and allowed to sit for 30 minutes. Another 1 L of acetone was added, mixed, and then vacuum filtered. The solids were washed with 1 L of hot acetone and then allowed to dry which yielded 320.0 g of product. The final product consisted of 74% of hydroxyethylcellulose and 26% of octadecyl moieties by weight and was insoluble in water. On average, one octadecyl group was present per 1.5 glucose moieties as determined by proton NMR.

Low Ratio Octadecyl Functionalized HEC

A similar reaction was run using 10.9 g Ashland HEC LOT#J0106 and 1.7 g octadecyl isocyanate in 60 mL toluene. The system was purged with argon stream for 40 minutes and the heating mantel was set to bring the system to reflux. After 3 hours of reflux, roughly 0.25 mL of water was removed. After 6 hours of reflux, ~0.6 mL of water was removed. The flask was allowed to cool to room temperature and was flushed with argon.

Under the same conditions as described above, dibutyltin dilaurate was added, followed by dropwise addition 1.7 g of octadecyl isocyanate. The reaction was stirred and allowed to run overnight, after which, the solution somewhat gelled. An additional 50 mL of toluene was added to reduce the viscosity solution which was then poured onto glass frit and rinsed with toluene. The product was then rinsed with 300 mL acetone. The remaining solids were taken up in acetone and again poured onto a frit, filtered, and rinsed with 100 mL acetone and then allowed to dry. The final weight of product was 12.1 g. The mass balance gave 1.2 g octadecyl isocyanate reacted with the HEC and proton NMR indicated a number density of 1 stearyl per ~12 glucose units.

This lower substituted variation product was initially very hydrophobic and suspended itself in a distinct layer when mixed in water. To observe ultrasonic induced hydrogel behavior, 0.25 g of this product was dispersed in 15 mL water using one drop of Tween 20. The product was sonicated for 15 seconds after which the segregated suspension was transformed into a water swelled gel.

Butyl Functionalized HEC

A 250 mL heavy wall glass flask was flamed dried and flooded with argon. To the flask was added a Dean-Stark trap, condenser, and a magnetic stir bar To the flask was added 10.4 g of hydroxyethyl cellulose (Ashland Chemical, LOT#J0106) followed by 13 mL of toluene. The flask was then place into an oil bath on a hot plate/stirrer and stirred under argon atmosphere. The temperature was raised until a strong reflux resulted. The toluene was refluxed for 6 hours during which 0.7 mL of water was removed.

The system was then cooled to ~80° C. and dibutyltin dilaurate (0.02 g, 0.03 mmol, Aldrich LOT#MKBK0920V) was added by syringe followed by 1.2 g of butyl isocyanate (98%, 12.1 mmol, Aldrich LOT #SHBB1574V). The system was heated to 90-95° C. for 12 hours followed by 105-110° C. for 4 hours. The toluene became very viscous. The system was then cooled to 60° C., added to 40 mL acetone and 50 mL toluene, and mixed. The HEC was filtered and washed with hot acetone followed and allowed to dry yielding 11.2 g product. On average there was one butyl group per four glucose moieties as determined by proton NMR.

Octyl Functionalized HEC

A 250 mL heavy wall glass flask was flamed dried and flooded with argon. To the flask was added a Dean-Stark trap, condenser, and a magnetic stir bar To the flask was added 10.4 g of hydroxyethylcellulose (Ashland Chemical, LOT#J0106) followed by 135 mL of toluene. The flask was then placed into an oil bath on a hot plate/stirrer and stirred under argon atmosphere. The temperature was raised until a strong reflux resulted. The toluene was refluxed for 6 hours during which 0.7 mL of water was removed.

The reaction was then cooled to ~80° C. and dibutyltin dilaurate (0.02 g, 0.03 mmol, Aldrich LOT#MKBK0920V) was added by syringe followed by 1.2 g of octyl isocyanate (98%, 7.7 mmol, Aldrich). The system was heated to 90-95° C. for 12 hours followed by 105-110° C. for 4 hours. The toluene became very viscous. The system was then cooled to 60° C., added to 40 mL acetone and 50 mL toluene, and mixed. The product was filtered and washed with hot acetone and allowed to dry yielding 11.2 g of product. On average there was one octyl group per 6.6 glucose moieties as determined by proton NMR.

This product was not readily soluble in water and was initially very hydrophobic. After several days in suspension, the aggregates began to absorb water in a manner unlike normal HEC gel formation. The particulates did not fully dissolve but became discreet translucent gel-like phases.

A lower substitution density octyl-HEC material was synthesized with a 1:22 ratio as determined by proton NMR. This material was readily soluble in water in a similar manner compared to normal HEC dissolution behavior. At a higher substitution number density of one octyl per one glucose the substance was insoluble and exhibited no swelling in water.

Dodecyl Functionalized HEC

A 250 mL heavy wall glass flask was flamed dried and flooded with argon. To the flask was added a Dean-Stark trap, condenser, and a magnetic stir bar To the flask was added 11.4 g of hydroxyethylcellulose (Ashland Chemical, LOT#J0106) followed by 145 mL of toluene. The flask was then placed into an oil bath on a hot plate/stirrer and stirred under argon atmosphere. The temperature was raised until a strong reflux resulted. The toluene was refluxed for 6 hours during which 0.7 mL of water was removed.

The reaction was then cooled to ~80° C. and dibutyltin dilaurate (0.02 g, 0.03 mmol, Aldrich LOT#MKBK0920V) was added by syringe followed by 1.2 g of dodecyl isocyanate (98%, 7.7 mmol, Aldrich, LOT#SHBC3408V). The system was heated to 90-95° C. for 12 hours followed by 105-110° C. for 4 hours. The toluene became very viscous. The system was then cooled to 60° C., added to 40 mL acetone and 50 mL toluene and mixed. The product was filtered and washed with hot acetone and allowed to dry yielding 11.8 g. On average there was one dodecyl group per ~10 glucose moieties, as determined by proton NMR. Dodecyl functionalization densities of 1:34 and 1:6 were also synthesized, as determined by proton NMR.

Figure 10:
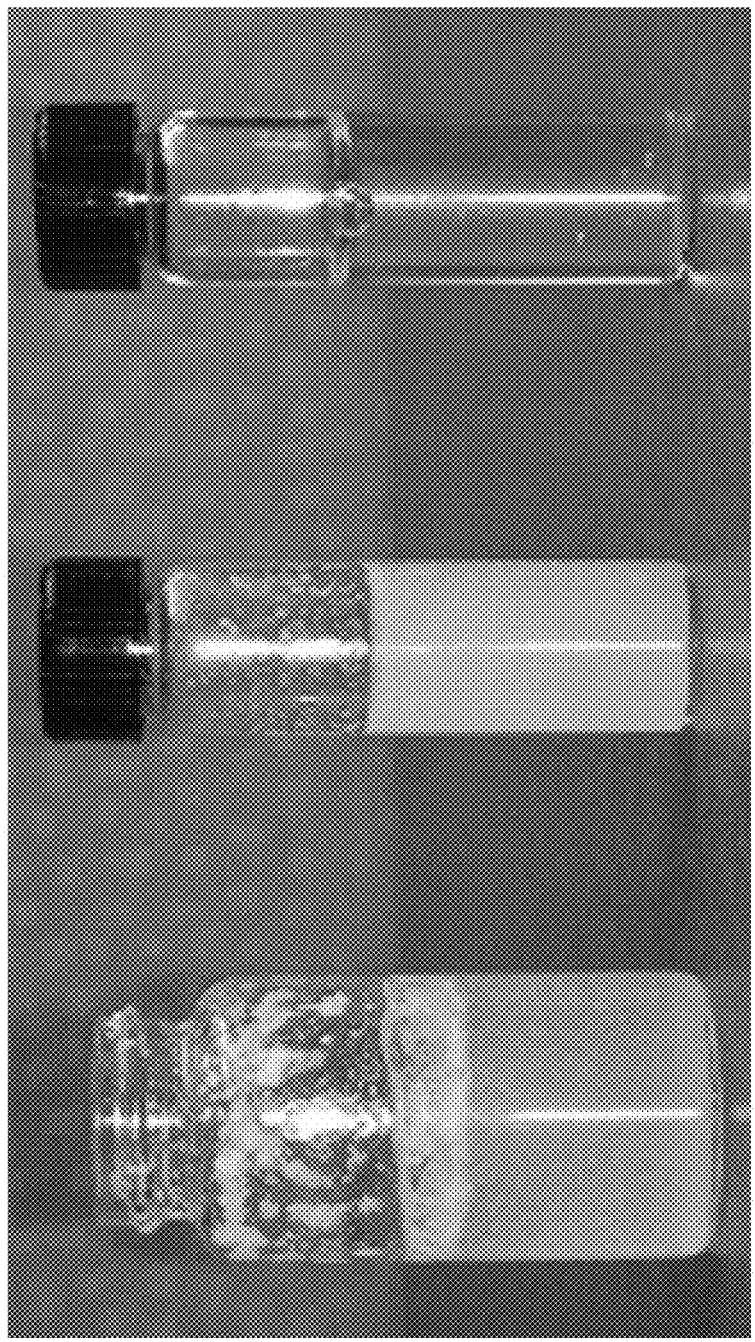
FIG. 10 is a photograph showing gelling behavior of embodiments of aggregates of the present disclosure.

In water these three variants show different degrees of gel/solubility behavior at quasi-equilibrium as shown in FIG. 10. Referring to FIG. 10, the vial at left contained a functionalized HEC having 1:6 dodecyl to glucose ratio and was completely insoluble (aggregates suspended in water); the middle vial contained a functionalized HEC having a 1:10 dodecyl to glucose ratio and exhibited a swelling behavior to provide a translucent gel; and the vial at right contained a functionalized HEC having a 1:34 ratio of dodecyl to glucose and was fully soluble.

Crosslinked Butyl Functionalized HEC

An additional variant of functionalized HEC was explored where photo/thermal initiated cross-linkable methacrylic pendants groups were substituted using isocyanate chemistry.

A 250 mL heavy wall glass flask was flamed dried and flooded with argon. To the flask was added a Dean-Stark trap, condenser, and a magnetic stir bar To the flask was added 13.6 g of hydroxyethylcellulose (Ashland Chemical, LOT#J0106) followed by 165 mL of toluene. The flask was then placed into an oil bath on a hot plate/stirrer and stirred under argon atmosphere. The temperature was raised until a strong reflux resulted. The toluene was refluxed for 6 hours during which 0.7 mL of water was removed.

The reaction was then cooled to ~80° C. and dibutyltin dilaurate (0.02 g, 0.03 mmol, Aldrich LOT#MKBK0920V) was added by syringe followed by 0.8 g of dodecyl isocyanate (98%, 5.1 mmol, Aldrich, LOT#SHBC3408V) and 0.5 g of 2-isocyanatoethyl methacrylate (3.2 mmol TCI America, LOT#V84IH-GP). The system was heated to 90-95° C. for 12 hours followed by 105-110° C. for 4 hours. The toluene became very viscous. The system was then cooled to 60° C., added to 40 mL acetone and 50 mL toluene, and mixed. The product was filtered and washed with hot acetone followed and allowed to dry yielding 11.8 g. On average there was one butyl group and one methacrylic group per ~7 glucose moieties as determined by proton NMR.

A 0.5 g quantity of this acrylic/butyl functionalized HEC was dissolved into 15 mL of de-ionized water. To this solution was added 0.01 g of 4,4-azobis(4-cyanovaleric acid) and allowed to dissolve and became a slightly viscous gel. The solution was heated to 65-70° C. and placed under a UV light. Over a period of 10 minutes the solution greatly increased in volume and transformed into a free-standing crosslinked hydrogel.

While illustrative embodiments have been illustrated and described, it will be appreciated that various changes can be made therein without departing from the spirit and scope of the disclosure.

The embodiments of the invention in which an exclusive property or privilege is claimed are defined as follows:

1. A composition, comprising:
   an aggregate including a core and a shell;
   the core consisting of a hydroxyethylcellulose; and
   the shell having a $C_{4-24}$ alkyl covalently bonded to the hydroxyethylcellulose of the core.

2. The composition of claim 1, wherein the $C_{4-24}$ alkyl is covalently bonded to the hydroxyethylcellulose via a linkage selected from carbamate linkage, an ester linkage, an ether linkage, and an amide linkage.

3. The composition of claim 1, further including a colorant selected from titanium oxide and iron oxide.

4. The composition of claim 1, further including a lipophilic carrier.

5. The composition of claim 1, wherein the aggregate is a reverse micelle.

* * * * *